(12) United States Patent
Burke et al.

(10) Patent No.: US 9,757,502 B2
(45) Date of Patent: Sep. 12, 2017

(54) CONTROL OF CIRCULATORY ASSIST SYSTEMS

(75) Inventors: David J. Burke, Concord, MA (US); Kevin Bourque, Reading, MA (US)

(73) Assignee: TCI LLC, St. Paul, MN (US)

( * ) Notice: Subject to any disclaimer, the term of this patent is extended or adjusted under 35 U.S.C. 154(b) by 601 days.

(21) Appl. No.: 13/242,248

(22) Filed: Sep. 23, 2011

(65) Prior Publication Data

US 2012/0078031 A1     Mar. 29, 2012

Related U.S. Application Data

(60) Provisional application No. 61/386,018, filed on Sep. 24, 2010, provisional application No. 61/472,241, filed on Apr. 6, 2011.

(51) Int. Cl.
*A61M 1/10*     (2006.01)
*A61M 1/12*     (2006.01)

(52) U.S. Cl.
CPC .......... *A61M 1/1086* (2013.01); *A61M 1/122* (2014.02); *A61M 1/101* (2013.01); *A61M 2205/3365* (2013.01)

(58) Field of Classification Search
None
See application file for complete search history.

(56) References Cited

U.S. PATENT DOCUMENTS

| | | | |
|---|---|---|---|
| 3,240,207 A | 3/1966 | Barker et al. | |
| 4,190,057 A | 2/1980 | Hill et al. | |
| 4,296,500 A | 10/1981 | Monties et al. | |
| 4,600,855 A | 7/1986 | Strachan | |
| 4,957,504 A | 9/1990 | Chardack | |
| 5,279,292 A | 1/1994 | Baumann et al. | |
| 5,289,821 A | 3/1994 | Swartz | |
| 5,385,581 A | 1/1995 | Bramm et al. | |
| 5,658,318 A | 8/1997 | Stroetmann et al. | |
| 5,693,091 A | 12/1997 | Larson et al. | |
| 5,715,837 A | 2/1998 | Chen | |
| 5,725,357 A | 3/1998 | Nakazeki et al. | |
| 5,798,454 A | 8/1998 | Nakazeki et al. | |
| 5,807,258 A | 9/1998 | Cimochowski et al. | |

(Continued)

FOREIGN PATENT DOCUMENTS

| | | |
|---|---|---|
| EP | 499939 A1 | 8/1992 |
| EP | 445782 B1 | 8/1994 |

(Continued)

OTHER PUBLICATIONS

Authorized Officer Trudy Hinterwimmer, PCT Search Report and Written Opinion for Application No. PCT/US2011/052912 mailed Dec. 19, 2011, 13 pages.

(Continued)

*Primary Examiner* — Erica Lee
(74) *Attorney, Agent, or Firm* — Kilpatrick Townsend & Stockton LLP

(57) ABSTRACT

In one general aspect, a method includes measuring blood flow through a right rotary blood pump, measuring blood flow through a left rotary blood pump, and controlling a speed of one of the rotary blood pumps using a controller that calculates the speed of one of the rotary blood pumps based on the measured blood flow through the other rotary blood pump.

29 Claims, 9 Drawing Sheets

(56) References Cited

U.S. PATENT DOCUMENTS

| | | | |
|---|---|---|---|
| 5,888,242 A | 3/1999 | Antaki et al. | |
| 6,027,498 A | 2/2000 | Mutch et al. | |
| 6,048,363 A | 4/2000 | Nagyszalanczy et al. | |
| 6,053,873 A | 4/2000 | Govari et al. | |
| 6,066,086 A | 5/2000 | Antaki et al. | |
| 6,139,487 A * | 10/2000 | Siess | A61M 1/101 415/900 |
| 6,142,752 A | 11/2000 | Akamatsu et al. | |
| 6,171,253 B1 | 1/2001 | Bullister et al. | |
| 6,176,822 B1 | 1/2001 | Nix et al. | |
| 6,264,601 B1 | 7/2001 | Jassawalla et al. | |
| 6,277,078 B1 | 8/2001 | Porat et al. | |
| 6,293,901 B1 | 9/2001 | Prem | |
| 6,367,333 B1 | 4/2002 | Bullister et al. | |
| 6,409,674 B1 | 6/2002 | Brockway et al. | |
| 6,422,990 B1 | 7/2002 | Prem | |
| 6,443,884 B1 | 9/2002 | Miyawaki | |
| 6,481,292 B1 | 11/2002 | Reich | |
| 6,540,658 B1 * | 4/2003 | Fasciano et al. | 600/17 |
| 6,547,753 B1 | 4/2003 | Plunkett et al. | |
| 6,623,420 B2 | 9/2003 | Reich et al. | |
| 6,636,769 B2 | 10/2003 | Govari et al. | |
| 6,669,624 B2 | 12/2003 | Frazier | |
| 6,716,189 B1 | 4/2004 | Jarvik et al. | |
| 6,736,980 B2 | 5/2004 | Moscaritolo | |
| 6,742,999 B1 | 6/2004 | Nüsser et al. | |
| 6,890,303 B2 | 5/2005 | Fitz | |
| 6,949,066 B2 | 9/2005 | Bearnson et al. | |
| 6,969,345 B2 | 11/2005 | Jassawalla et al. | |
| 6,974,436 B1 | 12/2005 | Aboul et al. | |
| 6,991,595 B2 * | 1/2006 | Burke et al. | 600/17 |
| 7,147,604 B1 | 12/2006 | Allen et al. | |
| 7,160,242 B2 | 1/2007 | Yanai | |
| 7,175,588 B2 | 2/2007 | Morello | |
| 7,211,048 B1 | 5/2007 | Najafi et al. | |
| 7,396,327 B2 | 7/2008 | Morello | |
| 7,578,782 B2 | 8/2009 | Miles et al. | |
| 7,645,255 B2 | 1/2010 | Gordon et al. | |
| 7,850,594 B2 | 12/2010 | Sutton et al. | |
| 7,861,582 B2 | 1/2011 | Miyakoshi et al. | |
| 7,963,905 B2 | 6/2011 | Salmonsen et al. | |
| 8,123,669 B2 | 2/2012 | Siess et al. | |
| 8,506,471 B2 | 8/2013 | Bourque | |
| 8,657,875 B2 | 2/2014 | Kung et al. | |
| 8,961,388 B2 | 2/2015 | Bourque | |
| 2002/0183628 A1 | 12/2002 | Reich et al. | |
| 2003/0023255 A1 | 1/2003 | Miles et al. | |
| 2003/0045772 A1 | 3/2003 | Reich et al. | |
| 2003/0074144 A1 | 4/2003 | Freed et al. | |
| 2003/0199727 A1 | 10/2003 | Burke et al. | |
| 2004/0034272 A1 | 2/2004 | Diaz et al. | |
| 2005/0071001 A1 | 3/2005 | Jarvik | |
| 2005/0107658 A1 | 5/2005 | Brockway | |
| 2005/0131271 A1 * | 6/2005 | Benkowski et al. | 600/16 |
| 2005/0159639 A1 | 7/2005 | Skliar et al. | |
| 2006/0047205 A1 | 3/2006 | Ludomirsky et al. | |
| 2006/0155158 A1 | 7/2006 | Aboul | |
| 2006/0229488 A1 | 10/2006 | Ayre et al. | |
| 2006/0241335 A1 | 10/2006 | Benkowski et al. | |
| 2007/0073393 A1 * | 3/2007 | Kung et al. | 623/3.13 |
| 2007/0083077 A1 | 4/2007 | Frazier | |
| 2007/0142923 A1 | 6/2007 | Ayre et al. | |
| 2007/0282210 A1 | 12/2007 | Stern | |
| 2008/0154095 A1 | 6/2008 | Stubkjaer et al. | |
| 2008/0281146 A1 | 11/2008 | Morello | |
| 2008/0319544 A1 | 12/2008 | Yaegashi | |
| 2009/0099406 A1 | 4/2009 | Salmonsen et al. | |
| 2009/0138080 A1 | 5/2009 | Siess et al. | |
| 2009/0156885 A1 | 6/2009 | Morello et al. | |
| 2010/0152526 A1 | 6/2010 | Pacella et al. | |
| 2010/0222632 A1 | 9/2010 | Poirier | |
| 2010/0222633 A1 | 9/2010 | Poirier | |
| 2010/0222634 A1 | 9/2010 | Poirier | |
| 2010/0222635 A1 | 9/2010 | Poirier | |
| 2010/0222878 A1 | 9/2010 | Poirier | |
| 2011/0054239 A1 | 3/2011 | Sutton et al. | |
| 2011/0112354 A1 | 5/2011 | Nishimura et al. | |
| 2013/0289336 A1 | 10/2013 | Bourque | |
| 2014/0275727 A1 | 9/2014 | Bonde et al. | |

FOREIGN PATENT DOCUMENTS

| | | |
|---|---|---|
| EP | 1046403 A1 | 10/2000 |
| EP | 1354606 A1 | 10/2003 |
| EP | 2298375 A1 | 3/2011 |
| EP | 2 618 862 A | 7/2013 |
| EP | 2 618 863 A | 7/2013 |
| GB | 2152241 A | 7/1985 |
| JP | 58054929 A | 4/1983 |
| JP | 04504673 | 8/1992 |
| JP | 09276397 | 10/1997 |
| JP | 2002224066 A | 8/2002 |
| JP | 2003/501180 A | 1/2003 |
| JP | 2004510482 | 4/2004 |
| JP | 2005514962 | 5/2005 |
| JP | 2008543378 | 12/2008 |
| JP | 2009297174 A | 12/2009 |
| JP | 2013-540005 A | 10/2013 |
| JP | 2013-240006 A | 11/2013 |
| TW | 201219072 A1 | 5/2012 |
| TW | 201221160 A1 | 6/2012 |
| WO | WO9215239 A1 | 9/1992 |
| WO | WO9959652 A1 | 11/1999 |
| WO | WO0069490 A1 | 11/2000 |
| WO | 0076288 A2 | 12/2000 |
| WO | WO 00/76822 A1 | 12/2000 |
| WO | WO0112070 A1 | 2/2001 |
| WO | WO0172352 A2 | 10/2001 |
| WO | WO03015609 A2 | 2/2003 |
| WO | WO2004028593 A1 | 4/2004 |
| WO | WO2005006975 A1 | 1/2005 |
| WO | WO 2005/051838 | 6/2005 |
| WO | WO2006133409 A2 | 12/2006 |
| WO | WO2009150893 A1 | 12/2009 |
| WO | WO 2012/040544 A1 | 3/2012 |
| WO | WO 2012/040551 A1 | 3/2012 |

OTHER PUBLICATIONS

U.S. Non-Final Office Action for U.S. Appl. No. 12/394,205 dated Jan. 19, 2012, 26 pages.

Authorized Officer Philip Jones, PCT Search Report and Written Opinion for Application No. PCT/US2011/052897 mailed Feb. 1, 2012, 17 pages.

Non-Final Office Action for U.S. Appl. No. 12/394,317 dated Feb. 15, 2012, 37 pages.

Non-Final Office Action for U.S. Appl. No. 12/394,244 dated Mar. 29, 2012, 21 pages.

Egemen Tuzun et al., "The Effect of Intermittent Low Speed Mode Upon Aortic Valve Opening in Calves Supported with a Jarvik 2000 Axial Flow Device," ASAIO Journal 2005; 51:139-143.

Authorized Officer Trudy Hinterwimmer, PCT Invitation to Pay Additional Fees for Application No. PCT/US2011/052897 mailed Dec. 13, 2011, 5 pages.

"Speed modulation of the continuous-flow total artificial heart to simulate a physiologic arterial pressure waveform" by Akira Shiose et al. in ASAIO Journal Sep./Oct. 2010—vol. 56—Issue 5—pp. 403-409. (published online Sep. 7, 2010).

"Flow Modulation Algorithms for Continuous Flow Left Ventricular Assist Devices to Increase Vascular Pulsatility: A Computer Simulation Study" by Mickey Ising, Sean Warren, Michael A. Sobieski, Mark S. Slaughter, Steven C. Koenig and Guruprasad A. Giridharan, Cardiovascular Engineering and Technology vol. 2, No. 2, 90-100, DOI: 10.1007/s13239-011-0042-x (Mar. 26, 2011).

Adam R. Travis et al, "Vascular pulsatility in patients with a pulsatile- or continuous-flow ventricular assist device," The Journal of Thoracis and Cardiovascular Surgery, vol. 133, No. 2, Feb. 2007, pp. 517-524.

Stijn Vandenberghe et al., "Hemodynamic Modes of Ventricular Assist with a Rotary Blood Pump: Continuous, Pulsatile, and Failure," ASAIO Journal 2005, vol. 51; pp. 711-718.

(56) References Cited

OTHER PUBLICATIONS

Kiyotaka Fukamachi et al., "An innovative, sensorless, pulsatile, continuous-flow total artificial heart: Device design and initial in vitro study," The Journal of Heart and Lung Transplantation, vol. 29, No. 1, Jan. 2010, pp. 13-20.
Hassan A. Khalil et al., "Induced pulsation of a continuous-flow total artificial heart in a mock circulatory system," The Journal of Heart and Lung Transplantation, vol. 29, No. 5, May 2010, pp. 568-573.
Yubing Shi et al., "Numerical Simulation of Cardiovascular Dynamics With Left Heart Failure and In-series Pulsatile Ventricular Assist Device," Artificial Organs, vol. 30, No. 12, 2006, pp. 929-948.
Yubing Shi et al., "Numerical Modeling of Hemodynamics with Pulsatile Impeller Pump Support," Annals of Biomedical Engineering, vol. 38, No. 8, Aug. 2010. (published online Mar. 16, 2010).
Tuzun et al., "The Effect of Intermittent Low Speed Mode Upon Aortic Valve Opening in Calves Supported With a Jarvik 2000 Axial Flow Device," ASAIO Journal, 2005, 51(2):139-143.
Bullister et al., "Physiologic control algorithms for rotary blood pumps using pressure sensor input," Artif Organs, 2002, 26(11):931-938.
Ednick et al., "Telemetric recording of intrapleural pressure," Journal of Surgical Research, 2007, 138(1):10-14.
Ellozy et al., "First Experience in Human Beings With a Permanently Implantable Intrasac Pressure Transducer for Monitoring Endovascular Repair of Abdominal Aortic Aneurysms," J Vasc Surg., 2004, 40:405-412.
Ferreira et al., "A rule-based controller based on suction detection for rotary blood pumps," Conf Proc IEEE Eng Med Biol Soc., 2007, pp. 3978-3981.
Giridharan et al., "Control Strategy for Maintaining Physiological Perfusion with Rotary Blood Pumps," Artif Organs, 2003, 27:639-648.
Haj-Yahia et al., "Midterm experience with the Jarvik 2000 axial flow left ventricular assist device," J Thorac Cardiovasc Surg., 2007, 134:199-203.
Letsou et al., "Is native aortic valve commissural fusion in patients with long-term left ventricular assist devices associated with clinically important aortic insufficiency?" The Journal of Heart and Lung Transplantation, 2006, 25 (4):395-399.
Ohuchi et al., "Control strategy for rotary blood pumps," Artif Organs., 2001, 25(5):366-370.
Reesink et al., "Suction due to left ventricular assist: implications for device control and management," Artif Organs, 2007, 31(7):542-549.
Rozenman, "Wireless Acoustic Communication With a Miniature Pressure Sensor in the Pulmonary Artery for Disease Surveillance and Therapy of Patients With Congestive Heart Failure," J Am Coll Cardiol., 2007, 49(7):784-789.
Voigt et al., "Suction Detection for the MicroMed DaBakey Left Ventricular Assist Device," ASAIO Journal, 2005, 51 (4):321-328.
Vollkron et al., "Development of a reliable automatic speed control system for rotary blood pumps," The Journal of Heart and Lung Transplantation, 2005, 24(11):1878-1885.
Vollkron et al., "Development of a suction detection system for axial blood pumps," Artif Organs, 2004, 28 (8):709-716.
Final Office Action issued on Sep. 20, 2011 in U.S. Appl. No. 12/394,185, 7 pages.
U.S. Notice of Allowance for U.S. Appl. No. 13/241,831 dated Apr. 2, 2013, 18 pages.
PCT International Preliminary Report on Patentability for International Application No. PCT/US2011/052897 dated Mar. 26, 2013, 12 pages.
Australian Patent Examination Report No. 2 for Application No. 2010217856 dated Mar. 15, 2013, 3 pages.
PCT International Preliminary Report on Patentability for International Application No. PCT/US2011/052912 dated Mar. 26, 2013, 9 pages.
U.S. Notice of Allowance for U.S. Appl. No. 13/241,831 dated May 7, 2013, 10 pages.
ROC (Taiwan) Pat. Appln. No. 100134484, Office Action mailed Jan. 13, 2014 with English translation.
U.S. Appl. No. 14/592,630 filed on Jan. 8, 2015 by Bourque. (Unpublished Copy available via USPTO's IFW System).
English Translation and Notice of Reasons for Rejection for corresponding Japanese Application No. 2013-530346 mailed on Oct. 30, 2014, 8 pages.
Requirement for Restriction/Election for U.S. Appl. No. 13/241,831 mailed on Feb. 6, 2013, 8 pages.
Non-Final Office Action for U.S. Appl. No. 13/926,044 mailed on Jun. 4, 2014, 10 pages.
Final Office Action for U.S. Appl. No. 13/926,044 mailed on Oct. 10, 2014, 6 pages.
Notice of Allowance for U.S. Appl. No. 14/261,817 mailed on Oct. 9, 2014, 9 pages.
Notice of Allowance for U.S. Appl. No. 13/926,044 mailed on Dec. 19, 2014, 6 pages.
Corrected Notice of Allowance for U.S. Appl. No. 14/261,817 mailed on Dec. 29, 2014, 4 pages.
Corrected Notice of Allowance for U.S. Appl. No. 13/926,044 mailed on Feb. 13, 2015, 4 pages.
EP11768210.4 , "Office Action", mailed Jul. 3, 2015, 3 pages.
JP2013-530341 , "Office Action", mailed May 20, 2015, 5 pages.

* cited by examiner

CONTROL OF CIRCULATORY ASSIST SYSTEMS

CROSS-REFERENCE TO RELATED APPLICATIONS

This application claims priority to and the full benefit of U.S. Provisional Application Ser. No. 61/386,018, filed Sep. 24, 2010, and titled "Generating Artificial Pulse" and U.S. Provisional Application Ser. No. 61/472,241, filed Apr. 6, 2011, and titled "Control of Circulatory Assist Systems," the entire contents of which are incorporated herein by reference.

TECHNICAL FIELD

This disclosure relates to control of circulatory assist systems.

BACKGROUND

Heart assist devices or pumps can be inserted in the circulatory system to pump blood from either ventricle or atrium of a heart to the vasculature. A pump supplementing a ventricle is known as a ventricular assist device, or VAD. A VAD is useful when the ventricle alone is incapable of providing adequate blood flow. A pump can also completely replace the function of a ventricle. It is known to use two blood pumps, one assisting or replacing the right ventricle and one assisting or replacing the left ventricle.

SUMMARY

In one general aspect, a blood pump controller can set the motor speed of a blood pump based on blood flow through another blood pump. One blood pump can support a left ventricle and the other blood pump can support a right ventricle.

In another general aspect, a blood pump controller for controlling right and left rotary blood pumps includes an input interface configured to receive a signal indicating blood flow through a right rotary blood pump and a signal indicating blood flow through a left rotary blood pump. The blood pump controller includes a processing unit configured to calculate a speed of one of the rotary blood pumps based on the blood flow through the other blood pump, and to control one of the rotary blood pumps to operate at the calculated speed.

In another general aspect, a controller for a heart assist system includes a processing unit configured to generate a pulsatility index for a right blood pump, set a speed of the right blood pump based on the pulsatility index for the right blood pump, generate a pulsatility index for a left blood pump, and set a speed of the left blood pump based on the pulsatility index for the left blood pump.

In another general aspect, a method of controlling blood flow includes measuring blood flow through a right rotary blood pump, measuring blood flow through a left rotary blood pump, and controlling a speed of one of the rotary blood pumps using a controller that calculates the speed of one of the rotary blood pumps based on the measured blood flow through the other rotary blood pump.

Implementations can include one or more of the following features. For example, the left blood pump supplies blood to a vasculature; the right blood pump supplies blood to a pulmonary system; and controlling a speed of one of the blood pumps using a controller that calculates the speed of one of the blood pumps based on the measured blood flow of the other blood pump includes controlling a speed of one of the blood pumps such that the blood flow through the right rotary blood pump is less than the blood flow through the left rotary blood pump. Controlling a speed of one of the blood pumps such that the blood flow through the right rotary blood pump is less than the blood flow through the left rotary blood pump includes controlling a speed of one of the blood pumps such that the blood flow through the right rotary blood pump is less than the blood flow through the left rotary blood pump by a minimum percentage of blood flow.

Implementations can also include one or more of the following features. For example, controlling a speed of one of the blood pumps using a controller that calculates the speed of one of the blood pumps based on the measured blood flow of the other blood pump includes determining that the measured blood flow through the right rotary blood pump has changed or that the measured blood flow through the left rotary blood pump has changed; and in response to determining that the measured blood flow through the right rotary blood pump has changed or that the measured blood flow through the left rotary blood pump has changed, adjusting the speed of the one of the blood pumps based on the measured blood flow through the other blood pump.

Implementations can also include one or more of the following features. For example, controlling a speed of one of the rotary blood pumps using a controller that calculates the speed of one of the rotary blood pumps based on the measured blood flow through the other rotary blood pump includes determining that a predetermined relationship between the measured blood flow through the right rotary blood pump and the measured blood flow through the left rotary blood pump is not satisfied; and in response to determining that the predetermined relationship is not satisfied, adjusting the speed of one of the rotary blood pumps such that the predetermined relationship is achieved. Controlling a speed of one of the rotary blood pumps using a controller that calculates the speed of one of the rotary blood pumps based on the measured blood flow through the other rotary blood pump includes determining that the measured blood flow through one of the rotary blood pumps exceeds a threshold; and reducing the speed of one of the blood pumps such that the measured blood flow is reduced below the threshold.

Implementations can also include one or more of the following features. For example, while controlling the speed of one of the rotary blood pumps using the controller that calculates the speed of one of the rotary blood pumps based on the measured blood flow through the other rotary blood pump, the speed of the other rotary blood pump can be controlled to generate a pulsatile flow. Operating a selected blood pump of the rotary blood pumps at a first speed for a first period of time; reducing the speed of the selected blood pump from the first speed to a second speed; operating the selected blood pump at the second speed for a second period of time; reducing the speed of the selected blood pump from the second speed to a third speed; operating the selected blood pump at the third speed for a third period of time; and increasing the speed of the selected blood pump from the third speed to the first speed. Controlling one of the rotary blood pumps to generate a rate of pressure change that simulates a natural physiologic pulse. Controlling one of the rotary blood pumps to generate a rate of pressure change that simulates a natural physiologic pulse includes changing the operating speed of one of the rotary blood pumps from a first speed to a second speed higher than the first speed such that the operating speed overshoots the second speed to produce the rate of pressure change that simulates a pressure change of a natural physiologic pulse.

In another general aspect, a method of controlling a heart assist system includes calculating a pulsatility index for a right blood pump, the right blood pump supporting a right ventricle, controlling the speed of the right blood pump based on the pulsatility index for the right blood pump, calculating a pulsatility index for a left blood pump, the left blood pump supporting a left ventricle, and controlling the speed of the left blood pump based on the pulsatility index for the left blood pump.

Implementations can include one or more of the following features. For example, the right blood pump is a rotary pump, and the left blood pump is a rotary pump. The pulsatility index for the right blood pump indicates a load on the right ventricle experienced during contraction of the right ventricle, and the pulsatility index for the left blood pump indicates a load on the left ventricle experienced during contraction of the left ventricle. Each pulsatility index (PI) is calculated over a control interval according to the following equation: $PI=(Q_{max}-Q_{min})/Q_{ave}$, where $Q_{max}$ is a maximum flow rate through the pump in the control interval, $Q_{min}$ is a minimum flow rate through the pump in the control interval, and $Q_{ave}$ is an average flow rate through the pump over the control interval. Measuring blood flow through the right blood pump, measuring blood flow through the left blood pump, and controlling a speed of one of the rotary blood pumps based on the measured blood flow through the other blood pump.

Implementations can also include one or more of the following features. For example, determining whether the blood flow through one of the blood pumps exceeds a flow threshold, and controlling the speed of the right blood pump and controlling the speed of the left blood pump include, when the pulsatility index for the right blood pump is below a first target level and the pulsatility index for the left blood pump is below a second target level: when the blood flow through the one of the blood pumps does not exceed the flow threshold, decreasing the speed of the right blood pump and decreasing the speed of the left blood pump, and when the blood flow through the one of the blood pumps exceeds the flow threshold, maintaining the speed of the right blood pump and maintaining the speed of the left blood pump. Controlling a speed of one of the rotary blood pumps based on the measured blood flow through the other blood pump includes determining that a relationship between the measured blood flow through the right blood pump and the measured blood flow through the left blood pump is not satisfied, and in response to determining that the relationship is not satisfied, adjusting the speed of the one of the blood pumps such that the relationship is achieved.

Implementations can also include one or more of the following features. For example, controlling the speed of the right blood pump is further based on the pulsatility index for the left blood pump. Controlling the speed of the left blood pump is further based on the pulsatility index for the right blood pump. Detecting a heart rate, and controlling the speed of the right blood pump is further based on the heart rate, and controlling the speed of the left blood pump is further based on the heart rate. Determining whether the heart rate exceeds a threshold heart rate, and controlling the speed of the right blood pump and controlling the speed of the left blood pump include, when the pulsatility index for the right blood pump is below a first target level and the pulsatility index for the left blood pump is below a second target level: when the heart rate does not exceed the threshold heart rate, decreasing the speed of the right blood pump and decreasing the speed of the left blood pump, and when the heart rate exceeds the threshold heart rate, maintaining the speed of the right blood pump and maintaining the speed of the left blood pump.

Implementations can also include one or more of the following features. For example, operating one of the blood pumps to produce an artificially induced pulsatile blood flow and calculating the corresponding pulsatility index for the blood pump that produces the artificially induced pulsatile flow such that data influenced by artificial blood flow variations of the artificially induced pulsatile blood flow are excluded from the calculating the corresponding pulsatility index. Operating the left blood pump to produce an artificially induced pulsatile blood flow, and calculating the left pulsatility index such that data influenced by artificial blood flow variations of the artificially induced pulsatile blood flow are excluded from calculating the left pulsatility index.

Implementations can also include one or more of the following features. For example, after controlling the speed of the right blood pump based on the pulsatility index for the right blood pump for a first period of time, controlling the speed of the right blood pump to generate a rate of pressure change that simulates a natural physiologic pulse. After controlling the speed of the left blood pump based on the pulsatility index for the left blood pump, controlling the speed of the left blood pump to generate a rate of pressure change that simulates a natural physiologic pulse. Alternating control of the left blood pump or the right blood pump between (i) control based on a pulsatility index and (ii) control to generate a rate of pressure change that simulates a natural physiologic pulse. Repeating a cycle that includes: controlling a selected blood pump of the blood pumps based on the corresponding pulsatility index for a first period of time; and controlling the selected blood pump to generate a pulsatile flow during a second period of time. Controlling the selected blood pump to generate a pulsatile flow during a second period of time includes controlling the selected blood pump to generate a rate of pressure change that simulates a natural physiologic pulse during the second period of time. Controlling the selected blood pump to generate a rate of pressure change that simulates a natural physiologic pulse for a second period of time includes generating the rate of pressure change that simulates the natural physiologic pulse by changing an operating speed of the selected pump from a first speed to a second speed higher than the first speed such that the operating speed overshoots the second speed.

Implementations can also include one or more of the following features. For example, controlling the selected pump to generate a pulsatile flow during a second period of time includes: operating a selected blood pump of the rotary blood pumps at a first speed for a first period of time; reducing the speed of the selected blood pump from the first speed to a second speed; operating the selected blood pump at the second speed for a second period of time; reducing the speed of the selected blood pump from the second speed to a third speed; operating the selected blood pump at the third speed for a third period of time; and increasing the speed of the selected blood pump from the third speed to the first speed. Operating a selected pump of the blood pumps to generate a pulsatile flow, including: operating the selected blood pump to produce a first blood flow rate through the selected blood pump associated with the relatively low pressure portion of the pulsatile blood flow, operating the selected blood pump to produce a second blood flow rate through the selected blood pump associated with the relatively high pressure portion of the pulsatile blood flow, and controlling the selected blood pump to increase a blood flow rate through the selected blood pump from the first flow rate to the second flow rate to produce the rate of pressure change that mimics the rate of pressure change of the natural physiologic pulse.

Implementations can also include one or more of the following features. For example, increasing the speed of the selected blood pump from the third speed to the first speed includes increasing the speed of the selected blood pump from the third speed to a fourth speed, operating the selected blood pump at the fourth speed for a fourth period of time, and increasing the speed of the selected blood pump from the fourth speed to the first speed. The second period of time is longer than a sum of the first period of time and the third period of time. Operating the selected blood pump at the first speed, reducing the speed of the selected blood pump from the first speed to the second speed, operating the selected blood pump at the second speed, reducing the speed of the selected blood pump from the second speed to the third speed, operating the selected blood pump at the third speed, and increasing the speed of the selected blood pump from the third speed to the first speed comprise a cycle, and pumping blood in a pulsatile manner further includes repeating the cycle. The duration of the second period of time is greater than half of the duration of the cycle. Operating the selected blood pump at the second speed for the second period of time includes operating the selected blood pump to produce a blood flow rate that has a predetermined relationship relative to an average blood flow rate for the cycle. Operating the selected blood pump at the second speed for the second period of time includes operating the selected blood pump to produce a blood flow substantially the same as the average blood flow rate for the cycle.

Implementations can also include one or more of the following features. For example, one or more of reducing the speed of the selected blood pump from the first speed to a second speed, reducing the speed of the selected blood pump from the second speed to a third speed, and increasing the speed of the selected blood pump from the third speed to the first speed includes one or more of a step-wise reduction in speed and a curvilinear reduction in speed. Operating the selected blood pump at the second speed includes operating the selected blood pump at the second speed during at least a portion of a contraction of a ventricle of human heart that is in blood flow communication with the selected blood pump. Pumping blood in a pulsatile manner also includes determining, based on a relationship between a speed of the selected blood pump and a power consumption of the selected blood pump, a synchronization between operating the impeller at the second speed and contraction of a ventricle of a human heart that is in blood flow communication with the selected blood pump. A generated pulsatile blood flow includes a temporal rate of change of blood pressure that approximates a temporal rate of change of blood pressure of a physiologic pulse. One or more of reducing the speed of the selected blood pump from the first speed to a second speed, reducing the speed of the selected blood pump from the second speed to a third speed, and increasing the speed of the selected blood pump from the third speed to the first speed includes generating a drive signal at a first time to produce a corresponding change in operating speed at a desired time. The second period of time is greater than the first period of time.

The details of one or more implementations are set forth in the accompanying drawings and the description below. Other features, objects, and advantages will be apparent from the description and drawings, and from the claims.

DETAILED DESCRIPTION

In a system with two blood pumps, a controller dynamically adjusts the speed of at least one of the pumps to maintain a relationship between the blood flow through the pumps. As physiological conditions of the patient change, the speed of at least one of the pumps is automatically adjusted to maintain the relationship. Additionally, the speed of the blood pumps can be adjusted to maintain a target load on one or both ventricles supported by the blood pumps.

Figure 1:
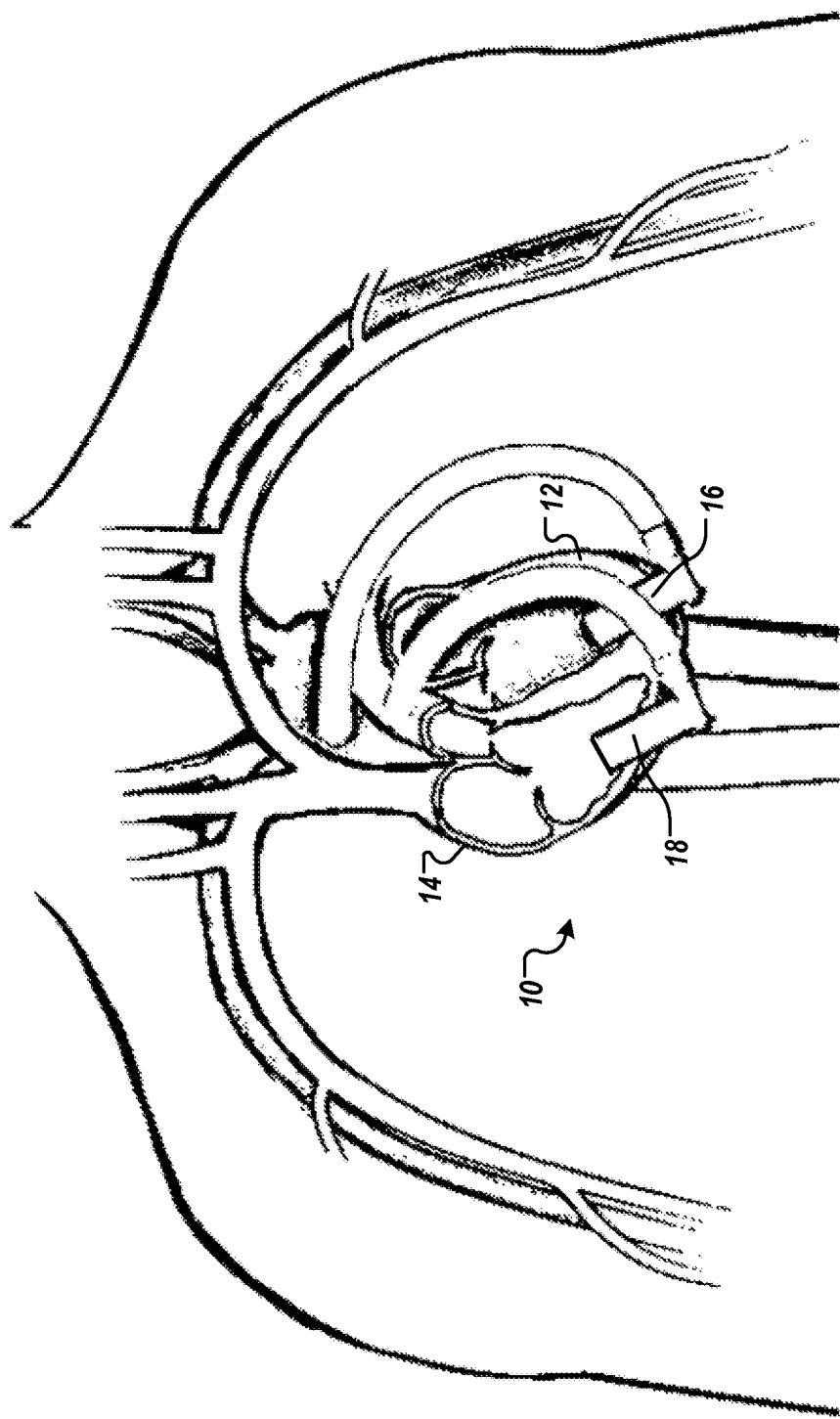
FIG. 1 is an illustration of a biventricular assist system including two blood pumps.

Referring to FIG. 1, a biventricular assist system 10 for treating, for example, a patient with a weakened left ventricle 12 and a weakened right ventricle 14, includes a left blood pump 16 and a right blood pump 18. The left blood pump 16 receives blood from the left ventricle 12 and supplies blood to the patient's vasculature. The right blood pump 18 receives blood from the right ventricle 14 and supplies blood to the patient's pulmonary system. The pumps 16, 18 are operated by independent control signals and can be independent units capable of being implanted separately.

As an alternative to the configuration of FIG. 1, rather than support weakened ventricles, the pumps 16, 18 can entirely replace the function of the left and right ventricles, respectively. For example, one or both of the ventricles can be removed, and the pump(s) can take over the function of the ventricle(s).

The pumps 16, 18 can be non-pulsatile pumps, for example, rotary pumps such as axial flow pumps or centrifugal pumps. In some implementations, one of the pumps is a centrifugal pump and the other pump is an axial flow pump. Each pump 16, 18 includes a motor. The motor speed of each pump 16, 18, which corresponds to the pump speed, is the dominant factor that affects blood flow through the pumps 16, 18. Thus the pump speed determines the level of support provided to the ventricles 12, 14 by the system 10. Also, as described further below, the pumps 16, 18 can be non-pulsatile pumps that are operated in an artificial pulse mode. In such case, the nature of the blood flow is a factor that affects the nature of support provided to the patient.

Figure 2:
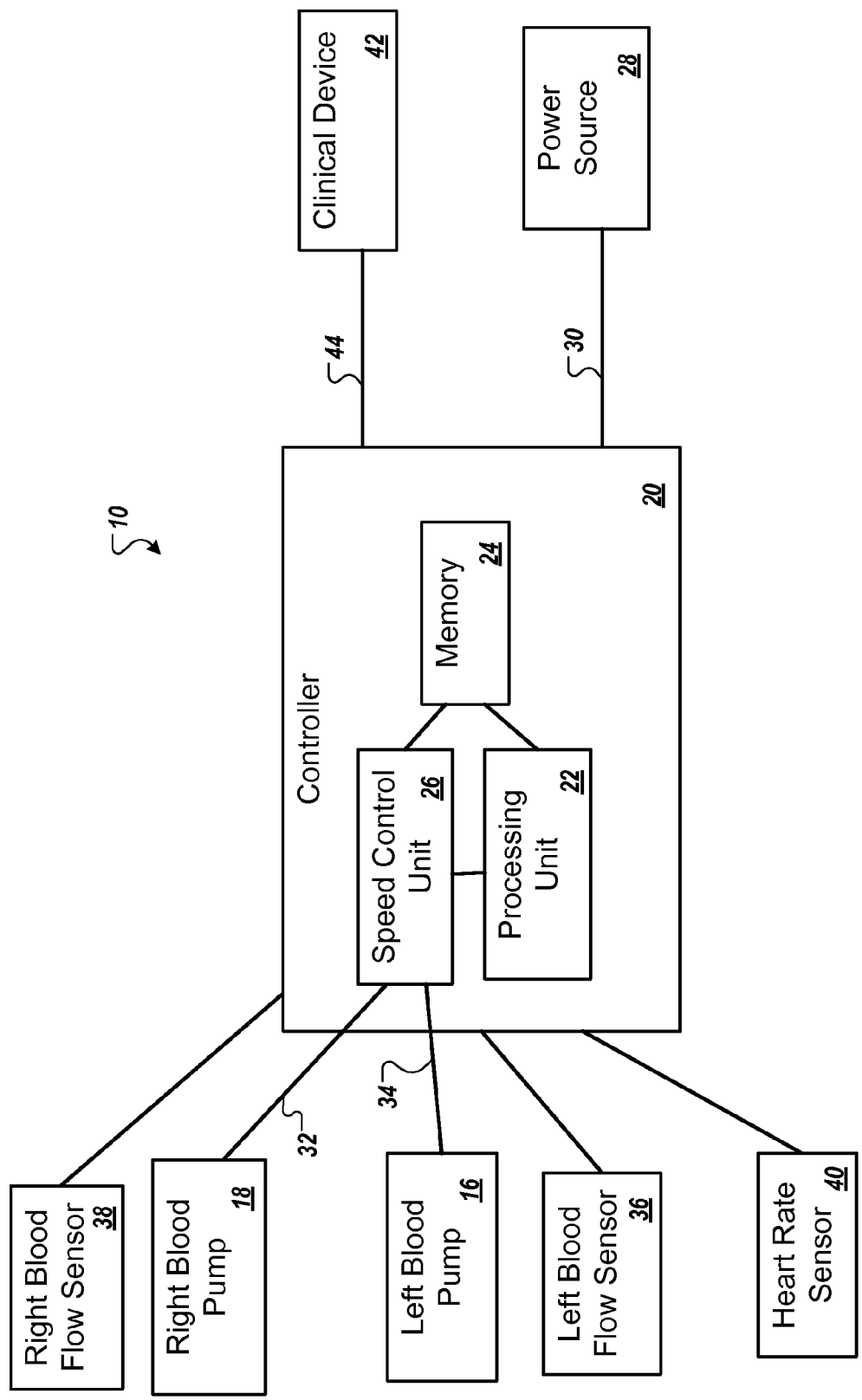
FIG. 2 is a block diagram of the biventricular assist system.

Referring to FIG. 2, the biventricular assist system 10 includes a controller 20 that controls the operation of the left blood pump 16 and the right blood pump 18. The controller 20 is implanted, for example, in the patient's abdomen near the pumps 16, 18. Alternatively, the controller 20 can reside outside of the patient's body. The controller 20 coordinates operation of the pumps 16, 18 and ensures that the circulatory needs of the patient are met. For example, the controller 20 sets the speed of each pump 16, 18 to provide a desired level of circulatory support. As physiological conditions of the patient change, the controller 20 varies the speed of the pumps 16, 18 to adjust the level of support provided. For example, the controller 20 increases the speed of the pumps 16, 18 to increase circulatory support when needed, and decreases the speed of the pumps 16, 18 to avoid dangerous conditions, such as inducing suction in one of the ventricles 12, 14.

The controller 20 can be implemented as a single device separate from the pumps 16, 18, can be integrated into one of the pumps 16, 18, or the functions performed by the controller 20 can be distributed among several different devices.

The controller 20 includes a processing unit 22 that calculates the appropriate speed for each pump 16, 18. The controller 20 includes memory 24 that stores target operating parameters for the pumps 16, 18 and results of calculations by the processing unit 22. The processing unit 22 can include one or more processing devices. The memory 24 also stores executable instructions that, when executed by the processing unit 22, cause the controller 20 to perform the operations described below, including calculating speeds for the pumps 16, 18 in response to changing conditions. Alternatively, the processing unit 22 can include fixed-function logic that performs control operations.

Input to the controller 20 can be received through an input interface (not shown) which can provide an interface to receive data from sensors, the blood pumps 16, 18, and other devices. Output from the controller 20 can be provided through an output interface (not shown) to, for example, a display or a computer system.

The controller 20 includes a speed control unit 26 that outputs control signals causing the pumps 16, 18 to operate at the speeds calculated by the processing unit 22. The speed control unit 26 communicates with the pumps 16, 18 over communication links 32, 34, which carry power and control signals. The speed control unit 26 varies a voltage or current supplied to the pumps 16, 18 to change the speed of the pumps 16, 18, which changes the flow of blood through the pumps 16, 18. The speed control unit 26 also measures operating conditions of the pumps 16, 18, such as current speed, power consumption, electrical current draw, and back electromotive force (BEMF) of the pumps 16, 18, which the processing unit 22 uses to calculate blood flow through the pumps 16, 18 and other operating parameters of the pumps 16, 18. The controller 20 sets the speed of the pumps 16, 18 independently, for example, using a different control signal to set the speed of each pump 16, 18.

The power consumed by the pumps 16, 18 is proportional to the speed of the motor of the pumps 16, 18, and thus proportional to the blood flow through the pumps 16, 18. The processing unit 22 calculates blood flow through the pumps 16, 18 using the current draw, rotational speed, and empirical constants known for a particular pump. Changes in power consumption or current draw by the pumps 16, 18 indicate changes in blood flow through the pumps 16, 18.

The system 10 includes a heart rate sensor 40 to measure the heart rate of the patient, a left blood flow sensor 36 to measure blood flow through the left blood pump 16, and a right blood flow sensor 38 to measure blood flow through the right blood pump 18. The controller 20, in addition to, or instead of measuring blood flow using pump operating data, measures blood flow through the pumps 16, 18 using outputs of the blood flow sensors 36, 38. In some implementations, pressure sensors can be included in addition to, or as an alternative to, the blood flow sensors 36, 38. Blood flow through the pumps 16, 18 can also be calculated based on the input of the pressure sensors.

The system 10 receives power from a power source 28, such as a battery or power conversion unit. The power source 28 is located outside the patient, and electrical power is transmitted to the system 10 through a percutaneous driveline 30 or through inductive coupling.

The controller 20 communicates with a clinical device 42 external to the patient. The controller 20 and the clinical device communicate via a telemetric interface 44, which may be wired or wireless. In some implementations, the telemetric interface 44 is integrated with the percutaneous driveline 30. Using the clinical device 42, a clinician can access current and historical information about the operation of the system 10 from the memory 24, and can perform diagnostics for the system 10.

Using the clinical device 42, the clinician can also input operating parameters for the system 10, including target levels of support for each of the ventricles 12, 14 as determined from examination of the patient. The clinician can input, for example, a desired pump speed, blood flow, and/or pulsatility index for one or both of the pumps 16, 18. The clinician can also select a control mode with which the controller 20 operates the pumps 16, 18, or enter new programming for the controller 20.

The controller 20 controls the operation of the pumps 16, 18 according to one of several different control modes. Using any of the different control modes, the controller 20 automatically sets the speed of one or both of the pumps 16, 18 to provide appropriate ventricular support as physiological conditions of the patient change. The control modes include, for example, controlling one or more of the pumps 16, 18 based on (1) blood flow through the pumps 16, 18, (2) a pulsatility index for one of the ventricles 12, 14, (3) a pulsatility index for each of the ventricles 12, 14 and a heart rate, and (4) a pulsatility index for each of the ventricles 12, 14 and blood flow through the pumps 16, 18. For the operation of the pumps 16, 18, both continuous operation and pulse-like operation modes can be implemented.

A pulse-like operation mode is also described below. The controller 20 can generate an artificial pulse by modulating a rotor speed of one of the blood pumps 16, 18. In some implementations, the control of a pump at a given time does not simultaneously include pulse-like operation and a control based on natural pulsatility of a ventricle 12, 14. For instance, the controller 20 can alternate control modes between the pulse mode and a continuous mode, or only one control mode can be selected for implementation. Implementation of pump control that alternates between control modes may be chosen based on a condition of the patient. The control modes can be changed, for example, hourly, daily, weekly, monthly, or according to a period having any duration in length ranging from minutes to weeks. Furthermore, it is possible to implement a pulse mode for one VAD that operates simultaneously with a continuous mode for another VAD. Moreover, if the ventricles are completely excised, either a fixed flow rate mode or a pulse mode of operation can be selected for either VAD.

In some implementations, both the pulsatility index control and the artificial pulse control are performed simultaneously. As described further below, the artificial pulse can be generated without interfering with the pulsatility index calculations. For example, the controller 20 can exclude data collected near the time of an artificial pulse perturbation from the pulsatility index calculation.

Examples of non-pulsatile control modes are described below, followed by examples of pulsatile control modes.

For each of the control modes described below, the controller 20 adjusts the speed of each pump 16, 18 in increments, for example, by increasing or decreasing pump speeds by a set amount, such as 100 rotations per minute (rpm). In the processes described in FIGS. 3 to 6, when the controller 20 adjusts a pump speed, the pump speed is adjusted by one increment. Later repetitions of the processes, occurring periodically, can further adjust the pump speeds. By gradually adjusting the speeds over time, the controller 20 detects the response of the patient's circulatory system and can prevent overcorrection of pump speeds.

The size of the increments can vary based on the characteristics of the pumps 16, 18, and the increments for the pumps 16, 18 can be different. The increments can be selected for each pump 16, 18 to effect a particular change in blood flow, such as a change of 0.1 liters/minute (l/min). As an example, at a given pressure, a change of 0.1 l/min may correspond to a change of 100 rpm for a first pump, and a change of 300 rpm for a second pump with different operating characteristics. Over the range of operation of the pumps 16, 18, the speed-flow response can be generally linear, allowing for a consistent increment for each pump 16, 18. In some implementations, the increments for each pump 16, 18 can be varied over the operating range to compensate for a non-linear flow response.

Because the output pressure for the right blood pump 18 is lower than the output pressure for the left blood pump 16, the speed change increment to effect a particular change in blood flow for the right blood pump 18 is typically less than the increment for the left blood pump 16. Thus when the pumps 16, 18 have the same operating characteristics, each incremental speed change for the left blood pump 16 is typically larger than the incremental speed change for the right blood pump 18.

To limit the risk of overpumping and suction, the controller 20 decreases pump speeds more quickly than the controller 20 increases pump speeds. Accordingly, the speed adjustment increments to decrease pump speed are greater than the speed adjustment increments to increase pump speed. For example, the increment to increase a pump speed may be 75 rpm, corresponding to a flow change 0.1 l/min, and the increment to decrease the pump speed may be 150 rpm, corresponding to a flow change of 0.2 l/min.

In some implementations, as an alternative to incremental adjustment, the controller 20 adjusts the speeds of the pumps 16, 18 according to known head and flow (HQ) characteristics of the pumps 16, 18 to reach a desired blood flow or blood pressure. The controller 20 calculates pump speeds to correspond to the desired blood flow or blood pressure and sets pumps 16, 18 to operate at the calculated speeds.

The controller 20 operates the pumps 16, 18 within a speed range, which is selected separately for each pump 16, 18. The upper and lower limits of the speed ranges are selected based on the prevailing condition of the patient's body and the patient's circulatory support needs. Typically, due to the higher output pressure facing the left blood pump 16, when the pumps 16, 18 have the same operating characteristics, the left blood pump 16 operates at speeds in a range higher than the range in which the right blood pump 18 operates, although the ranges may overlap.

The controller 20 also performs calculations to detect and avoid overpumping of the ventricles 12, 14, thus avoiding suction and/or distending of the ventricles 12, 14. The controller 20 determines the pumping state of the ventricles 12, 14 based on, for example, measured ventricular pressure, pump blood flow, and/or a pulsatility index (described below) for the ventricle 12, 14. For example, the controller 20 can detect and prevent suction of a ventricle using the techniques described in U.S. Pat. No. 6,991,595 and/or the techniques described in U.S. patent application Ser. No. 12/394,264, each of which is incorporated herein by reference in its entirety.

(1) Control Based on Blood Flow

In a flow-balancing control mode, the controller 20 sets the speed of one of the pumps 16, 18 such that a predetermined relationship between blood flow through the pumps 16, 18 is maintained. The controller 20 designates one of the pumps 16, 18 as a lead pump, and designates the other pump 16, 18 as a flow-balancing pump. The lead pump is operated at, for example, a fixed speed selected to provide a desired level of ventricular support. The controller 20 sets the speed of the flow-balancing pump based on blood flow through the lead pump.

Because the speed of the flow-balancing pump is automatically adjusted by the controller 20, the system 10 responds to changes in blood flow through the lead pump without manual adjustment by a clinician. The controller 20 also adjusts the speed of the flow-balancing pump when physiological conditions cause blood flow through the lead pump to change. Regardless of the control mode selected for the lead pump, the controller 20 varies the speed of the flow-balancing pump to maintain a predetermined relationship between blood flow through the flow-balancing pump and blood flow through the lead pump.

By contrast, the controller 20 sets the speed of the lead pump using a control mode independent of the speed of the flow-balancing pump and the blood flow through the flow-balancing pump. For example, the controller 20 may operate the lead pump at a fixed speed selected by a clinician. Alternatively, the controller 20 varies the speed of the lead pump such that blood flow through the lead pump is maintained at a target rate, or such that blood flow through the lead pump is maintained in a target range.

In some instances, if blood flow through the right blood pump 18 exceeds the blood flow through the left blood pump 16 for a significant period of time, blood can accumulate in the pulmonary system, causing the lungs to fill with fluid. To avoid this condition, known as pulmonary edema, the controller 20 can adjust the pump speeds such that, for example, blood flow through the left blood pump 16 (which is typically the lead pump) is greater than or equal to blood flow through the right blood pump 18 (which is typically the flow-balancing pump). The controller 20 can also set the pump speeds such that blood flow through the left blood pump 16 is greater than blood flow through the right blood pump 18 by a particular percentage, such as 10%, or a particular flow rate, such as 1.0 liters/minute. Typically, these relationships can be maintained regardless of which of the pumps 16, 18 operates as the lead pump or the flow-balancing pump.

In a normal heart, left ventricular output is typically greater than right ventricular output by about 10%. While the cardiac outputs fluctuate, the total right cardiac output should generally be maintained at or below about 90% of the total left cardiac output. In some implementations, the cardiac outputs from the left ventricle 12 and the right ventricle 14 are assumed to be equal. As a result, the controller 20 maintains blood flow through the right blood pump 18 at less than 90% of the blood flow through the left blood pump 16 to operate the system 10 safely.

Figure 3:
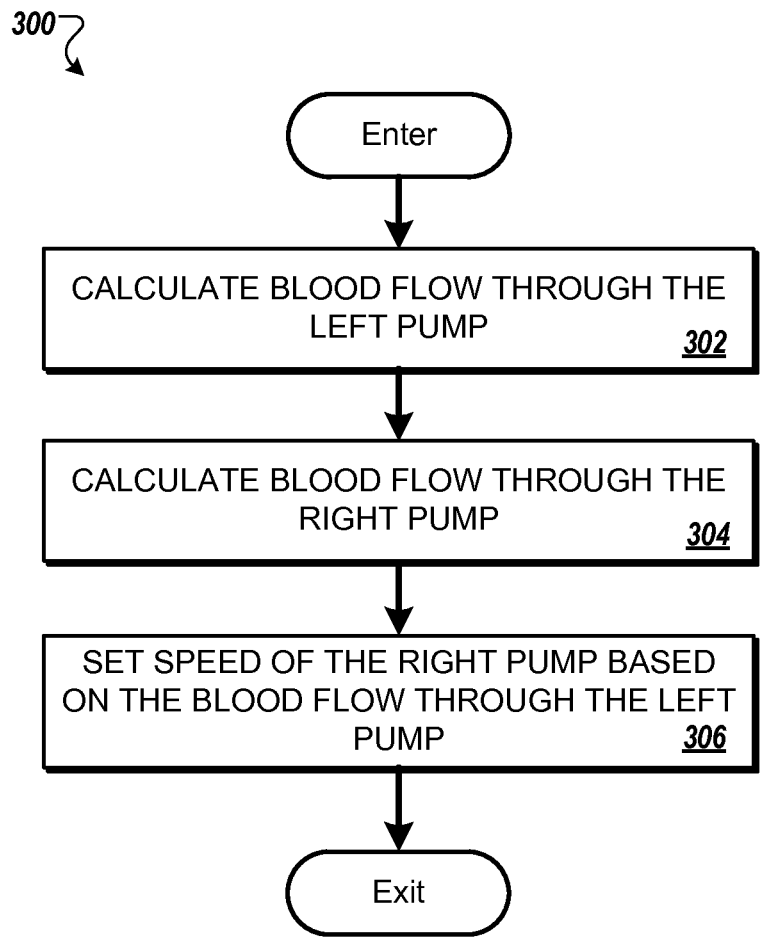
FIG. 3 is a flow diagram of a process for controlling one of the blood pumps based on blood flow.

Referring to FIG. 3, the controller 20 performs a process 300 to set the speed of the right blood pump 18, which, for instance, is designated as the flow-balancing pump. Generally, the left blood pump 16 is then operated as the lead pump. The speed of the right blood pump 18 is increased after blood flow through the left blood pump 16 has already increased, resulting in a low risk of blood flow increases above the desired level due to an increase in pump speed.

At the beginning of the process 300, in step 302, the controller 20 calculates blood flow through the left blood pump 16. In step 304, the controller 20 calculates blood flow through the right blood pump 18. The blood flow through each of the pumps 16, 18 is determined as described above, for example, measured using input from the blood flow sensors 36, 38 or calculated using rotational speed and current draw of the pumps 16, 18. The controller 20 determines average blood flow over an interval, such as 1 second, 5 seconds, or 15 seconds, and can also determine an instantaneous blood flow rate. In some implementations, rather than calculating absolute blood flow through the pumps 16, 18, the controller 20 calculates a relative measure of the blood flow using, for example, the relative current draw of the pumps 16, 18.

In step 306, the controller 20 sets the speed of the right blood pump 18 based on the blood flow through the left blood pump 16. For example, the controller 20 dynamically calculates a target blood flow for the right blood pump 18 at, for example, 90% of the blood flow through the left blood pump 16. The controller 20 then compares the target blood flow to the calculated blood flow through the right blood pump 18, and adjusts the speed of the right blood pump 18 up or down so that the target blood flow is achieved. If the blood flow through the right blood pump 18 is less than the target blood flow, the controller 20 increases the speed of the right blood pump 18. By contrast, if the blood flow through the right blood pump 18 is greater than the target blood flow, the controller 20 decreases the speed of the right blood pump 18.

Rather than determining a target blood flow, the controller 20 may compare the blood flow through the pump 16, 18 to determine whether a predetermined relationship is satisfied, for example, whether the blood flow through the right blood pump 18 is less than or within a particular range relative to the blood flow through the left blood pump 16. If the controller 20 determines that the relationship is not satisfied, the controller 20 adjusts the speed of the right blood pump 16 so that the relationship is achieved.

The controller 20 repeats the steps of the process 300 approximately once each second to update the speed of the flow-balancing pump and maintain the relative flow through the pumps 16, 18. In some implementations, the controller 20 repeats the process 300 a different periodic rate, substantially continuously, in response to detected changes in blood flow, or based on a measured number of heartbeats.

In some implementations, the speed of the flow-balancing pump is adjusted in response to determining that blood flow through one of the pumps has changed, rather than determining that the desired relationship between the flows is no longer satisfied. Thus the controller 20 can adjust the speed of the flow-balancing pump to maintain the desired flow relationship, without requiring the relationship to be lost before an adjustment is made.

(2) Control Based on a Pulsatility Index

Using a pulsatility index control mode, the controller 20 sets the speed of one of the pumps 16, 18 such that the corresponding ventricle 12, 14 experiences a desired load. The controller 20 designates one of the pumps 16, 18 as a lead pump, and adjusts the speed of the lead pump to maintain a calculated pulsatility index, discussed below, at a target level. As a result, the load on the ventricle remains substantially consistent, even as physiological conditions change. The controller 20 sets the speed of the other pump 16, 18 based on blood flow through the lead pump, using the flow balancing control mode described above.

The pulsatility of blood flow through a pump indicates the load experienced by a ventricle supported by the pump. Pulsatility refers to the amount of variation in blood flow through the pump. The pump experiences varying input pressures during the cardiac cycle, resulting in varying blood flow through the pump. Strong contractions of the ventricle result in large variations in blood flow during the cardiac cycle, or high pulsatility of blood flow through the pump. Weak contractions result in lower variations in blood flow, or lower pulsatility. High pulsatility indicates that a large amount of blood flows out of the ventricle during systole due to a strong contraction, whereas low pulsatility indicates that a smaller amount of blood flows out of the ventricle due to weak contraction.

The pulsatility of flow through the pump is correlated to the peak filling of the ventricle during the cardiac cycle. The greater the expansion and filling of a ventricle, the greater the force with which the ventricle contracts to eject the blood in the ventricle. Thus the pulsatility of flow through the pump, by indicating the force of contraction of the ventricle, also indicates the degree to which a ventricle fills with blood.

The controller 20 calculates a pulsatility index that indicates the difference between the maximum flow and the minimum flow through the pump during a particular time period. For example, the pulsatility index, PI, is be a dimensionless number calculated according to the equation, $PI=(Q_{max}-Q_{min})/Q_{ave}$, where $Q_{max}$ is a maximum flow rate through the pump in the period, $Q_{min}$ is a minimum flow rate through the pump in the period, and $Q_{ave}$ is an average flow rate through the pump over the period. The quantity $Q_{ave}$ is calculated, for example, as the midpoint between $Q_{max}$ and $Q_{min}$, or alternatively as the total volume divided by the length of the time period of interest.

The controller 20 uses the variation in current draw of the pump over a control interval to calculate the pulsatility index. Because the current draw of the pump is proportional to blood flow through the pump, variation in the current draw indicates the variation in blood flow. Alternatively, the controller 20 uses input from the blood flow sensors to calculate the pulsatility index.

The controller 20 calculates the pulsatility index over a time period called a control interval. The control interval has a duration of, for example, one second, in which approximately one to two heartbeat cycles occur. The control interval can also be varied, for example, with the speed of the heartbeat. The pulsatility index can be averaged over multiple control intervals. The controller 20 stores previous pulsatility indices and generates an average of previously calculated pulsatility indices, for example, an average of the pulsatility indices calculated for the previous fifteen control intervals.

When a pump supporting a ventricle operates at a fixed speed, the pump provides a generally fixed degree of ventricular unloading. As circulatory needs of the patient increase and the pump speed remains constant, the ventricle becomes increasingly filled with blood, resulting in the ventricle experiencing an increased load because the pump does not remove a sufficient amount of blood from the ventricle. Without adjustment of the pump speed, the ventricle may fill excessively because the ventricle is incapable of adjusting to the varying physiological conditions, for example, the ventricle may lack the ability to achieve a contraction sufficient to eject the increased amount of blood filling the ventricle.

To regulate the load on the ventricle, the controller 20 adjusts the speed of the pump using the calculated pulsatility index and a target pulsatility index. The target pulsatility index represents a desired level of load for the ventricle. When circulatory demands increase, causing the calculated pulsatility index to exceed the target pulsatility index, the controller 20 increases the speed of the pump to increase support, thus decreasing the load experienced by the ventricle and reducing the pulsatility index. Similarly, when the pulsatility index is below the target level, the controller 20 decreases the speed of the pump to increase the load experienced by the ventricle and thus increase the pulsatility index. Thus when physiological conditions change, rather than allowing the load on the ventricle to increase or decrease, the controller 20 adjusts the pump allow the load on the ventricle to remain substantially consistent under different physiological conditions. Generally, increasing the speed of a pump will increase ventricular unloading and thus reduce the pulsatility index. By contrast, decreasing the speed of a pump will permit increased loading in the ventricle and thus increase the pulsatility index.

Figure 4:
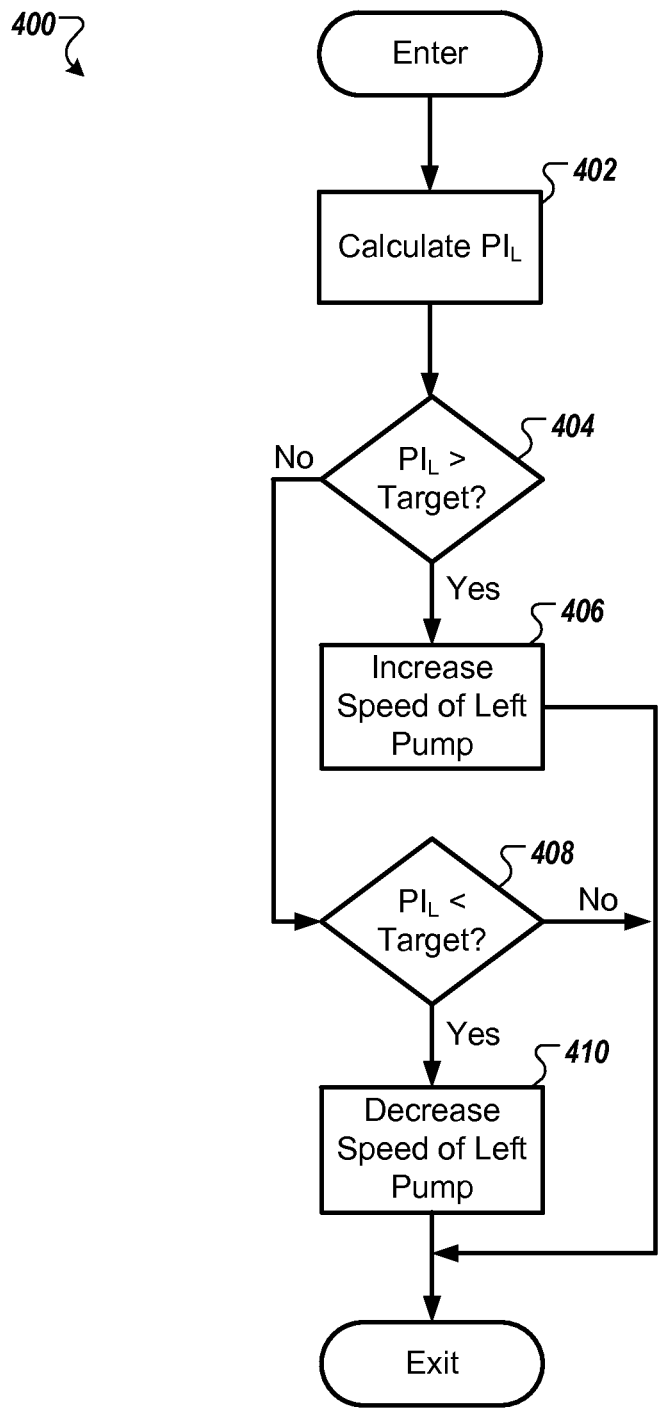
FIG. 4 is a flow diagram of a process for controlling one of the blood pumps based on a pulsatility index.

Referring to FIG. 4, the controller 20 performs a process 400 to control the left blood pump 16 as the lead pump based on a pulsatility index for the left ventricle 12. Independent of the process 400, the controller 20 also performs the process 300 (FIG. 3), setting the speed of the right blood pump 18 based on blood flow through the left blood pump 16. Generally, as described above, the left blood pump 16 is operated as the lead pump to limit the risk of pulmonary edema.

Beginning the process 400, in step 402, the controller 20 calculates a left pulsatility index, $PI_L$, for the left ventricle 12, which is an average of the pulsatility indices corresponding to the previous 15 control intervals. In step 404, the controller 20 determines whether the left pulsatility index, $PI_L$, is above a target pulsatility index, which corresponds to a particular load on the left ventricle 12. If the pulsatility index, $PI_L$, is greater than the target pulsatility index, the left ventricle 12 is experiencing a greater load than desired. In response, in step 406, the controller 20 increases the speed of the left blood pump 16 to increase support to the left ventricle 12, ending the process 400. The speed of the left blood pump 16 is increased by a set increment, such as 100 rpm. Increasing the speed of the left blood pump 16 causes the left ventricle 12 to become less filled during subsequent cardiac cycles, decreasing the load experienced by the ventricle 12 and reducing the pulsatility index, $PI_L$, toward the target pulsatility index.

If the controller 20 determines in step 404 that the left pulsatility index, $PI_L$, is not greater than the target pulsatility index, the controller 20 determines in step 408 whether the left pulsatility index, $PI_L$, is less than the target pulsatility index. If so, the left blood pump 16 is providing excessive support, causing the left ventricle 12 to be under-loaded. In response, the controller 20 decreases the speed of the left blood pump 16, ending the process 400. Decreasing the speed of the left blood pump 16 allows the left ventricle 12 to fill more completely and provide a greater portion of the circulatory output. To reduce the risk of suction of the left ventricle 12, the controller 20 decreases the speed in step 410 by a larger amount than the increase in speed in step 406, for example, by 200 rpm.

In step 408, if the left pulsatility index, $PI_L$, is not less than the target pulsatility index, the load experienced by the ventricle 12 and the level of support provided by the left blood pump 16 are appropriate. The controller 20 maintains the current speed of the left blood pump 16, ending the process 400.

The controller 20 repeats the process 400 to adjust the support provided by the lead pump to meet to the changing needs of the patient. In some implementations, the controller 20 performs the steps of the process 400 at a particular interval, for example, every 15 seconds. In some implementations, the pump speed is adjusted each time a pulsatility index for a control interval is calculated, using a running average of calculations for the previous 15 control intervals.

In some implementations, the controller 20 determines in step 404 and step 406, whether the pulsatility index, $PI_L$, is within a particular tolerance of the target pulsatility index. For example, the controller 20 determines whether the pulsatility index, $PI_L$, is within an upper or lower bound of a target pulsatility index range.

The techniques described can also be used to control the right blood pump 18 as the lead pump, and to control the left blood pump 16 as a flow-balancing pump. In this configuration, the speed of the right blood pump 18 is based on comparisons between a pulsatility index for the right ventricle 14 and a target pulsatility index for the right ventricle 14.

(3) Control Based on Two Pulsatility Indices and Heart Rate

Using a dual pulsatility index control mode, the controller 20 sets the speeds of both of the pumps 16, 18 to regulate the loads experienced by both ventricles 12, 14. The controller 20 adjusts the speeds of the pumps 16, 18 using a pulsatility index calculated for each ventricle 12, 14 and a target pulsatility index for each ventricle 12, 14. In addition, the controller 20 adjusts the speeds of the pumps 16, 18 by comparing a heart rate of the patient to a reference heart rate.

Figure 5:
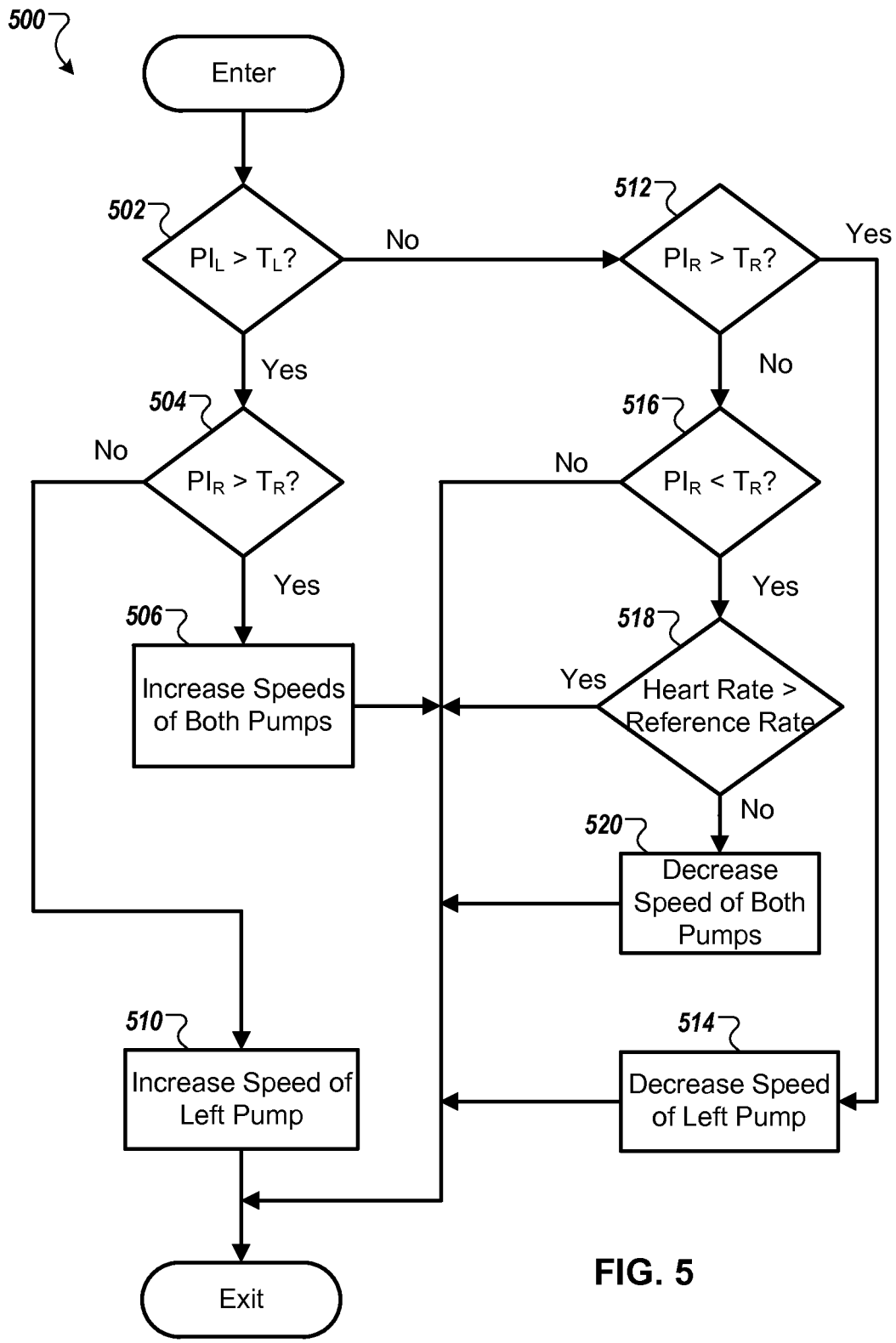
FIG. 5 is a flow diagram of a process for controlling both blood pumps based on two pulsatility indices and a heart rate.

Referring to FIG. 5, the controller 20 sets the speeds of the pumps 16, 18 by performing a process 500. In the process 500, the left blood pump 16 is operated as the lead pump of the system 10, and the speed of both pumps 16, 18 is adjusted based on the pulsatility indices for both ventricles 12, 14. The process 500 ends after the controller 20 adjusts the pump speeds or determines that the current pump speeds should be maintained. The process 500 is repeated to adjust the pumps as physiological conditions change.

The controller 20 sets the speed of the pumps 16, 18 using (i) a right pulsatility index, $PI_R$, for the right ventricle 14 and (ii) a left pulsatility index, $PI_L$, for the left ventricle 12. The controller 20 calculates the pulsatility indices, $PI_R$, $PI_L$, at the beginning of the process 500, or accesses the pulsatility indices, $PI_R$, $PI_L$, from stored values in the memory 24. The pulsatility indices, $PI_R$, $PI_L$, are averages of pulsatility index calculations for the 15 most recent control intervals.

The controller 20 stores (i) a target pulsatility index for the right ventricle 14, or right target, $T_R$, and (ii) a target pulsatility index for the left ventricle 12, or left target, $T_L$. The targets, $T_R$, $T_L$, indicate desired loads on the ventricles 12, 14, and in the process 500, the controller 20 varies the pump speeds to achieve the desired loads. Because the left blood pump 18 is the lead pump for the process 500, the left pulsatility index, $PI_L$, and the left target, $T_L$, influence the control of the system 10 to a greater degree than the right pulsatility index, $PI_R$, and the right target, $T_R$. For example, the system 10 is controlled with a higher priority to achieve the left target, $T_L$, than to achieve the right target, $T_R$. In addition, the speed of the left pump 16 can be increased or decreased without a corresponding change in the speed of the right pump 18. The speed of the right pump 18, however, changes only when the speed of the left pump 16 changes.

Beginning the process 500, in step 502, the controller 20 determines whether the left pulsatility index, $PI_L$, exceeds the left target, $T_L$. If so, the controller 20 determines in step 504 whether the right pulsatility index, $PI_R$, is greater than the right target, $T_R$. If so, then the system 10 is providing insufficient support to both ventricles 12, 14. As a result, in step 506 the controller 20 increases the speed of the left blood pump 16 and increases the speed of the right blood pump 18. Increasing the pump speeds off-loads the ventricles 12, 14 further and causes the pulsatility indices, $PI_R$, $PI_L$, to decrease toward the targets, $T_R$, $T_L$.

Returning to step 504, if the right pulsatility index, $PI_R$, is not greater than the right target, $T_R$, the controller 20 increases the speed of the left blood pump 16 in step 510, increasing support to the left ventricle 12. Increased support is needed because, as determined in step 502, the left pulsatility index, $PI_L$, exceeds the left target, $T_L$, indicating overloading of the left ventricle 12. By increasing the speed of the left blood pump 16, the load on the left ventricle is reduced and the pulsatility index, $PI_L$, decreases toward the target level, $T_L$.

Returning to step 502, if the left pulsatility index, $PI_L$, is greater than the left target, $T_L$, the controller 20 determines in step 512 whether the right pulsatility index, $PI_R$, is greater than the right target, $T_R$. If so, then the controller 20 decreases the speed of the left blood pump 16 in step 514. When entering step 514, the left pulsatility index, $PI_L$, is known to be at or below the left target, $T_L$, as determined in step 502. By decreasing the speed of the left blood pump 16, support for the left ventricle 12 is reduced, allowing the left pulsatility index, $PI_L$, to increase over subsequent calculations. Because the right ventricle 14 remains overloaded when the left ventricle 12 is under-loaded, it is assumed that reducing the speed of the left blood pump 16 to avoid left ventricular suction will not significantly affect the loading of the right ventricle 14.

If the outcome of step 512 is negative, the controller 20 determines in step 516 whether the right pulsatility index, $PI_R$, is less than the right target, $T_R$. If not, then the right ventricle 14 is experiencing an appropriate load, the controller 20 maintains the current speeds of the pumps 16, 18. If, however, the right pulsatility index, $PI_R$, is less than the right target, $T_R$, the controller 20 continues to step 518.

Entering step 518, comparisons between the pulsatility indices, $PI_R$, $PI_L$, and the targets, $T_R$, $T_L$, indicate that both ventricles 12, 14 are under-loaded, suggesting that support for the ventricles 12, 14 should be decreased. Nevertheless, the needs of the patient are not always fully indicated by the pulsatility indices, $PI_R$, $PI_L$. For example, when the patient begins to exercise, the patient's heart rate increases but the ventricles 12, 14 do not immediately expand. Net blood flow through the ventricles 12, 14 increases as the heart rate increases, but the pulsatility indices, $PI_R$, $PI_L$, for the pumps 16, 18 initially decrease. As the patient's needs for support are increasing due to the increased exertion, it is undesirable to decrease ventricular support.

To distinguish between actual under-loading of the ventricles 12, 14 and false indications of under-loading, the controller 20 compares a measured heart rate of the patient to a reference heart rate. The reference rate target is set at a level higher than a resting heart rate or an average heart rate for the patient. For example, the reference heart rate is set at an offset above a resting heart rate of the patient by a particular percentage, such as 10%, or a particular amount, such 10 beats per minute. In some implementations, the reference heart rate can be set based on a running average of the patient's heart rate over a time period. A baseline heart rate can be determined as an average rate over, for example, the previous hour, and the reference heart rate, for instance, can be set as an offset of 10 or 15 beats per minute above the baseline rate.

When the heart rate is above the reference rate, the exertion of the patient is likely above average, and the ventricular support should not be decreased. Thus when the controller 20 determines in step 518 that the patient's heart rate is above the reference rate the controller 20 maintains the speeds of the pumps 16, 18.

By contrast, when the heart rate is below the reference rate in step 518, the patient is most likely not exercising, and the ventricles 12, 14 are most likely under-loaded because the pumps 16, 18 are drawing too much blood from the ventricles 12, 14. As a result, the controller 20 continues to step 520 and decreases the speeds of both of the pumps 16, 18, allowing the loads experienced by the ventricles 12, 14 to increase.

The controller 20 repeats the process 500, adjusting the speeds of the pumps 16, 18 in response to changing physiological conditions. The controller 20 recalculates the pulsatility indices, $PI_R$, $PI_L$, and repeats the process 500 periodically to allow the patient's circulatory system to respond to the changes in ventricular support. Alternatively, the controller 20 repeats the process substantially continuously or as new values for the pulsatility indices, $PI_R$, $PI_L$, are calculated.

The process 500 is summarized as a set of control rules in Table 1, below. Table 1 includes columns indicating conditions for (i) the left pulsatility index, $PI_L$, (ii) the right pulsatility index, $PI_R$, and (iii) the heart rate of the patient. Table 1 also includes a column of actions performed by the controller 20 in response to the conditions in each row. The controller 20 performs the action in a given row of Table 1 when the conditions in the row are determined to be present.

TABLE 1

Control Rules for the Left Blood Pump 16 as Lead Pump (Process 500)

| Left Pulsatility Index ($PI_L$): | Right Pulsatility Index ($PI_R$): | Heart Rate: | Action |
|---|---|---|---|
| Above Left Target ($T_L$) | Above Right Target ($T_R$) | (any value) | Increase the speeds of both pumps 16, 18 |
| Above Left Target ($T_L$) | At or Below Right Target ($T_R$) | (any value) | Increase the speed of the left blood pump 16 |
| Below Left Target ($T_L$) | Above Right Target ($T_R$) | (any value) | Decrease the speed of the left blood pump 16 |
| Below Left Target ($T_L$) | At Right Target ($T_R$) | (any value) | Maintain current speeds of both pumps 16, 18 |
| Below Left Target ($T_L$) | Below Right Target ($T_R$) | Below Reference Heart Rate | Decrease the speeds of both pumps 16, 18 |
| Below Left Target ($T_L$) | Below Right Target ($T_R$) | Above Reference Heart Rate | Maintain current speeds of both pumps 16, 18 |

The controller 20 can also set the speeds of the pumps 16, 18 with the right blood pump 18 designated as the lead pump, using the control rules described in Table 2, below.

TABLE 2

Control Rules for the Right Blood Pump 18 as Lead Pump

| Right Pulsatility Index ($PI_R$) is: | Left Pulsatility Index ($PI_L$) is: | Heart Rate is: | Action |
|---|---|---|---|
| Above Right Target ($T_R$) | Above Left Target ($T_L$) | (any value) | Increase the speeds of both pumps 16, 18 |
| Above Right Target ($T_R$) | At or Below Left Target ($T_L$) | (any value) | Increase the speed of the right blood pump 18 |
| Below Right Target ($T_R$) | Above Left Target ($T_L$) | (any value) | Decrease the speed of the right blood pump 18 |
| Below Right Target ($T_R$) | At Left Target ($T_L$) | (any value) | Maintain current speeds of both pumps 16, 18 |
| Below Right Target ($T_R$) | Below Left Target ($T_L$) | Below Reference Heart Rate | Decrease the speeds of both pumps 16, 18 |
| Below Right Target ($T_R$) | Below Left Target ($T_L$) | Above Reference Heart Rate | Maintain current speeds of both pumps 16, 18 |

(4) Control Based on Two Pulsatility Indices and Blood Flow

Figure 6:
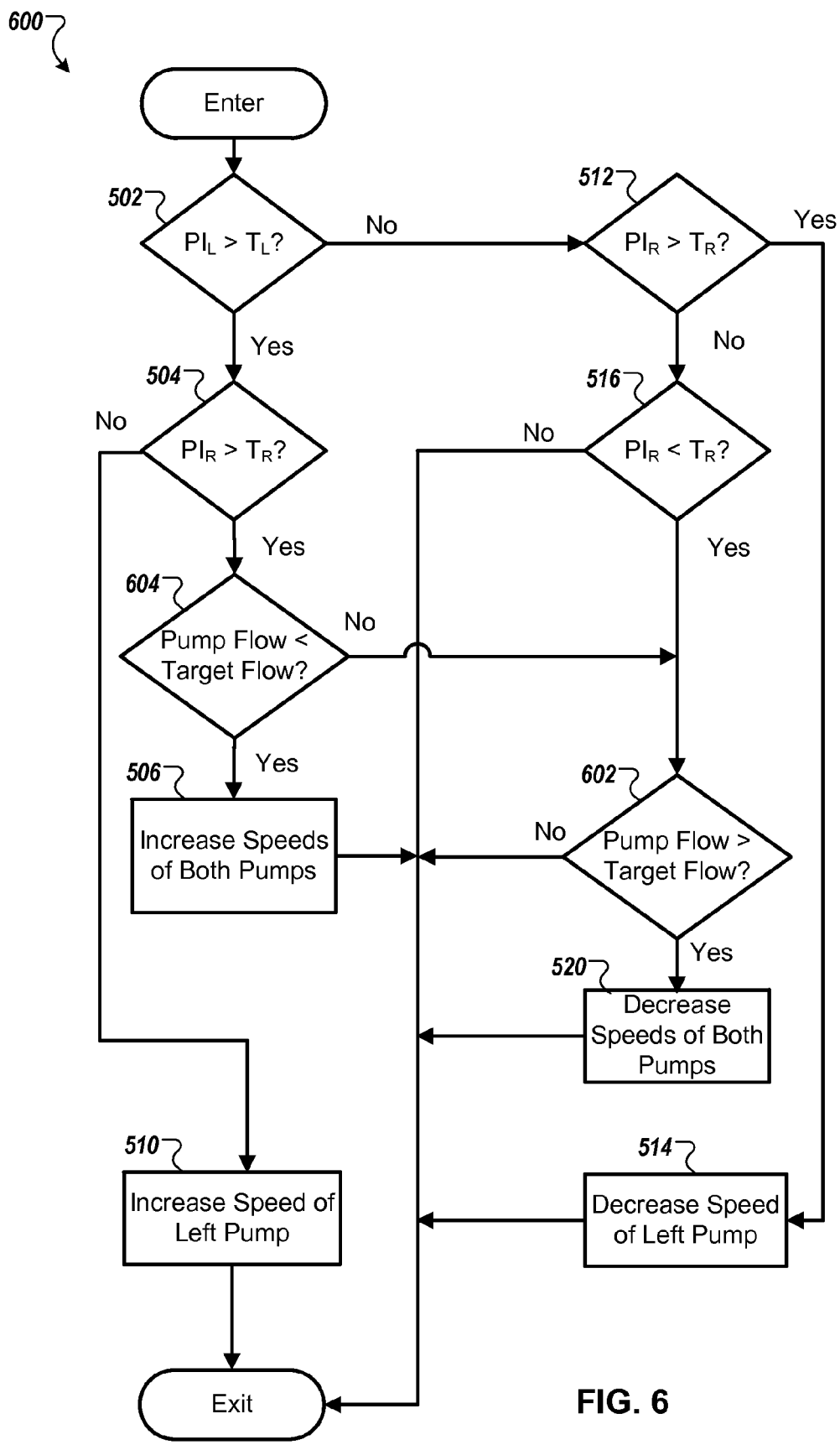
FIG. 6 is a flow diagram of a process for controlling both blood pumps based on two pulsatility indices and blood flow.

Referring to FIG. 6, the controller 20 performs a process 600 that implements an alternative control mode using the pulsatility indices, $PI_R$, $PI_L$, calculated for each ventricle 12, 14. Rather than comparing a heart rate to a reference heart rate, however, the controller 20 compares measured blood flow to a target blood flow to maintain a generally constant blood flow through the lead pump while regulating the load on the ventricles 12, 14.

In the process 600, the left blood pump 16 is operated as the lead pump. The pulsatility indices, $PI_R$, $PI_L$, are calculated and the targets, $T_R$, $T_L$, are set as described above for the process 500. The controller 20 additionally stores a target blood flow for the right blood pump 16.

The process 600 includes many of the same steps as the process 500. In the process 600, however, the step 518 of the process 500 for comparing a heart rate to a reference rate is replaced with step 602, in which blood flow through the lead pump 18 is compared to the target blood flow. The process 600 also includes an additional step 604, between steps 504 and 506, in which blood flow through the lead pump 18 is compared to the target blood flow.

At the point in the process 600 when step 602 is reached, both of the pulsatility indices, $PI_R$, $PI_L$, have been determined to be below their respective targets, $T_R$, $T_L$. Under these conditions, if blood flow through the left blood pump 16 is greater than the target blood flow, support for the ventricles 12, 14 should be reduced. The controller 20 reduces the speed of both blood pumps 16, 18, allowing the pulsatility indices, $PI_R$, $PI_L$, to rise toward the levels indicated by the targets, $T_R$, $T_L$, and reducing the potential of ventricular suction due to excessive unloading. In addition, reducing the speed of the pumps 16, 18 allows the blood flow through the left pump to decrease toward the target blood flow level.

By contrast, if blood flow through the left blood pump 16 is determined to be at or below the target blood flow, the speed of the pumps 16, 18 should not be reduced, because a reduction in speed would cause the blood flow through the left blood pump to decrease. The controller 20 maintains the speed of the pumps 16, 18 so that the current blood flow through the left pump 16 is maintained.

Referring now to step 604, when both ventricles 12, 14 experience a higher than desired load, the controller 20 compares the blood flow through the left blood pump 16 to the target blood flow. Step 604 is reached when the right pulsatility index, $PI_R$, exceeds the right target, $T_R$, and the left pulsatility index, $PI_L$, exceeds the left target, $T_L$. If the blood flow through the left blood pump 16 is less than the target blood flow, the controller 20 increases the speeds of both pumps 16, 18 to increase support to both ventricles 12, 14 and increase the blood flow through the left pump 16.

If blood flow through the left blood pump 16 is not less than the target blood flow, the controller determines in step 602 whether blood flow through the left blood pump 16 is greater than the target blood flow. If blood flow through the left blood pump 16 is greater than the target blood flow, the controller 20 reduces the speed of the pumps 16, 18. If not, the flow through the left blood pump 16 is at the target blood flow level, and the controller 20 maintains the current speed of the pumps 16, 18.

The controller 20 repeats the process 600, adjusting the speeds of the pumps 16, 18 in response to changing physiological conditions. For example, the controller 20 recalculates the pulsatility indices, $PI_R$, $PI_L$, and repeats the process 600 approximately once each second as new values for the pulsatility indices, $PI_R$, $PI_L$, are calculated. The process 600 can also be repeated at other intervals or performed substantially continuously.

In some implementations, the target blood flow is a moving average of blood flow over a particular interval rather than a fixed value. As a result, comparisons to the target blood flow indicate whether blood flow through the pump is increasing or decreasing. In step 602, for example, increasing blood flow through the left blood pump 16 is increasing can be a strong indication that the patient's level of activity is increasing, and thus that the speeds of the pumps 16, 18 should be maintained.

In some implementations, the blood flow through the right blood pump 18 is compared to a target blood flow, in addition to or instead of comparing blood flow through the left blood pump 16. The decisions in steps 602 and 604 can be based on blood flow through both pumps 16, 18 to achieve a target blood flow for the right blood pump 16 and a target blood flow for the left blood pump 16. For example, in step 602 the pump speeds can be maintained when either or both of the blood flows through the pumps 16, 18 are at or below their respective target blood flow.

The process 600 can be modified to additionally adjust the pump speeds based on measured a heart rate. The heart rate and blood flow can together be compared to target values to determine whether the patient's need for ventricular support is increasing. For example, in step 602, the controller 20 can determine whether the heart rate is above a reference rate and whether blood flow through one or both of the pumps 16, 18 is above the target blood flow. In some implementations, in step 602, the controller 20 maintains the current pump speeds unless the heart rate is below the reference rate and the blood flow is above the target blood flow, in which case the pump speeds are decreased.

The process 600 is summarized as a set of control rules in Table 3, below. Table 3 includes columns indicating conditions for (i) the left pulsatility index, $PI_L$, (ii) the right pulsatility index, $PI_R$, and (iii) the blood flow through the left blood pump 16. Table 3 also includes a column of actions performed by the controller 20 in response to the conditions in each row.

TABLE 3

Control Rules for the Left Blood Pump 16 as Lead Pump (Process 600)

| Left Pulsatility Index ($PI_L$) is: | Right Pulsatility Index ($PI_R$) is: | Blood Flow through left pump 16 is: | Action |
|---|---|---|---|
| Above Left Target ($T_L$) | Above Right Target ($T_R$) | At Blood Flow Target Level | Maintain current speeds of both pumps 16, 18 |
| Above Left Target ($T_L$) | Above Right Target ($T_R$) | Above Blood Flow Target Level | Decrease the speeds of both pumps 16, 18 |
| Above Left Target ($T_L$) | Above Right Target ($T_R$) | Below Blood Flow Target Level | Increase the speeds of both pumps 16, 18 |
| Above Left Target ($T_L$) | At or Below Right Target ($T_R$) | (any value) | Increase the speed of the left blood pump 16 |
| Below Left Target ($T_L$) | Above Right Target ($T_R$) | (any value) | Decrease the speed of the left blood pump 16 |
| Below Left Target ($T_L$) | At Right Target ($T_R$) | (any value) | Maintain current speeds of both pumps 16, 18 |
| Below Left Target ($T_L$) | Below Right Target ($T_R$) | Above Blood Flow Target Level | Decrease the speeds of both pumps 16, 18 |
| Below Left Target ($T_L$) | Below Right Target ($T_R$) | At or Below Blood Flow Target Level | Maintain current speeds of both pumps 16, 18 |

The controller 20 can also set the speeds of the pumps 16, 18 with the right blood pump 18 designated as the lead pump, using the control rules described in Table 4, below.

TABLE 4

Control Rules for the Right Blood Pump 18 as Lead Pump

| Right Pulsatility Index ($PI_R$) is: | Left Pulsatility Index ($PI_L$) is: | Blood Flow through right pump 18 is: | Action |
|---|---|---|---|
| Above Right Target ($T_R$) | Above Left Target ($T_L$) | At Blood Flow Target Level | Maintain current speeds of both pumps 16, 18 |
| Above Right Target ($T_R$) | Above Left Target ($T_L$) | Above Blood Flow Target Level | Decrease the speeds of both pumps 16, 18 |
| Above Right Target ($T_R$) | Above Left Target ($T_L$) | Below Blood Flow Target Level | Increase the speed of both pumps 16, 18 |
| Above Right Target ($T_R$) | At or Below Left Target ($T_L$) | (any value) | Increase the speed of the right blood pump 18 |
| Below Right Target ($T_R$) | Above Left Target ($T_L$) | (any value) | Decrease the speed of the right blood pump 18 |
| Below Right Target ($T_R$) | At Left Target ($T_L$) | (any value) | Maintain current speeds of both pumps 16, 18 |
| Below Right Target ($T_R$) | Below Left Target ($T_L$) | Above Blood Flow Target Level | Decrease the speeds of both pumps 16, 18 |
| Below Right Target ($T_R$) | Below Left Target ($T_L$) | At or Below Blood Flow Target Level | Maintain current speeds of both pumps 16, 18 |

Any of the four control modes described above can be used to control the pumps 16, 18 of the system 10 when the pumps 16, 18 are configured to support the ventricles 12, 14. When the pumps 16, 18 are configured to replace the right and left ventricles of a heart, however, only the flow balancing control mode is used. Without pulsating ventricles to provide varying input pressures to the pumps 16, 18, there is no variation of flow through the pumps 16, 18. As a result, pulsatility indices cannot be used as control parameters for the system 10 when the pumps 16, 18 replace the ventricles completely.

In some implementations, control can be implemented such that the left blood pump 16 and the right blood pump 18 operate independently unless the overpumping of a ventricle 12, 14 occurs. For example, each pump 16, 18 is operated a fixed speed or based on a pulsatility index without feedback between the pumps 16, 18. If overpumping occurs, which may lead to suction and serious disruptions of overall blood flow, control of the right blood pump 18 becomes limited based on the operation of the left blood pump 16.

In addition to, or as an alternative to, the techniques described above, the maximum speed of the right blood pump 18 can be limited so that the right blood pump cannot generate excessive outlet pressures that could cause pulmonary edema.

In some implementations, one or both of the pumps 16, 18 may be operated for periods of time to produce a pulsatile flow, as described below. For example, the operating speeds of the pumps 16, 18 can be varied in a manner that generates or intensifies a pulsatile flow through the pumps 16, 18.

The controller 20 can control one of the pumps 16, 18 to produce an artificial pulse where operation at a fixed or constant speed is described above. Control modes that induce an artificial pulsatile flow can be used in an alternating sequence with control modes that use pulsatility index calculations. As an example, the controller 20 can control one or both of the pumps 16, 18 in a manner that alternates between periods of pulsatile control and periods of control that generate substantially continuous flow. For example, the controller 20 can operate one or both of the pumps 16, 18 to generate a pulsatile flow during a first period. The controller 20 can then operate one or both of the pumps 16, 18 based on pulsatility index calculations or blood flow during a second period. The controller 20 alternates between the different control modes at predetermined intervals. The period of time that each control mode is active can have a predetermined duration.

In some implementations, the controller 20 operates one of the pumps 16, 18 to generate a pulsatile flow while operating the other pump 16, 18 to generate a substantially continuous flow. Substantially continuous flow can be generated using a control mode based on blood flow or a control mode based on pulsatility index calculations for a ventricle supported by the pump 16, 18 operated to generate the continuous flow. As an example, the controller 20 can operate one of the pumps 16, 18 using a pulsatile flow control mode, as described further below. The controller 20 can simultaneously operate the other pump 16, 18 such that a predetermined relationship between blood flow through the pumps 16, 18 is maintained, using the techniques described above.

Various characteristics of the artificial pulse may differ substantially from those of a physiologic pulse even while producing a response in the body that is similar to that caused by the physiologic pulse. It is generally understood that the dominant source of dissipated energy that characterizes a meaningful pulse is the pressure wave generated at the start of cardiac systole. Accordingly, the artificial pulse described herein can include a relatively brief perturbation of a nature designed to produce such dissipated energy.

In some implementations, an artificial pulse cycle includes a perturbation period that simulates the pulse pressure that occurs at the leading edge of systole of a physiologic pulse. The perturbation period can include, for example, a period during which the blood pump 16 is operated at a low speed, followed immediately by a period during which the blood pump 16 is operated at a higher speed. The artificial pulse cycle can also include a period longer than the perturbation period during which the pump 16 is operated at an intermediate speed, for example, a speed maintained between the speeds realized during the perturbation period.

Operating the pump at the intermediate speed can contribute to a high operating efficiency. The efficiency achieved can be greater than, for example, the efficiency of a pump that only alternates between equal periods of operation at a high speed and at a low speed. Typically, a continuous flow pump operates with highest efficiency near the middle of its rotational speed range. Therefore, it can be advantageous to operate such a pump at or near a mid-range speed for at least a portion of an artificial pulse cycle.

Some of the parameters that affect physiologic phenomena include pulse pressure and the rate of blood pressure change (dp/dt). For the blood pump 16, for example, pulse pressure and time variation in blood pressure are affected by the angular velocity of the rotor. Thus, the blood pump 16 can be selectively controlled to produce a pulsatile blood flow pattern, including a desired pulse pressure and/or a desired rate of pressure change, by producing a pump speed pattern that includes a time period of relatively high rotor rotation speeds and a time period of relatively low rotor rotation speeds. In some implementations, the pulse pressure produced by the blood pump 16 or produced by the blood pump 16 and the patient's heart in combination can be approximately 10 mmHg or more, such as from approximately 20 mmHg to approximately 40 mmHg.

Figure 7:
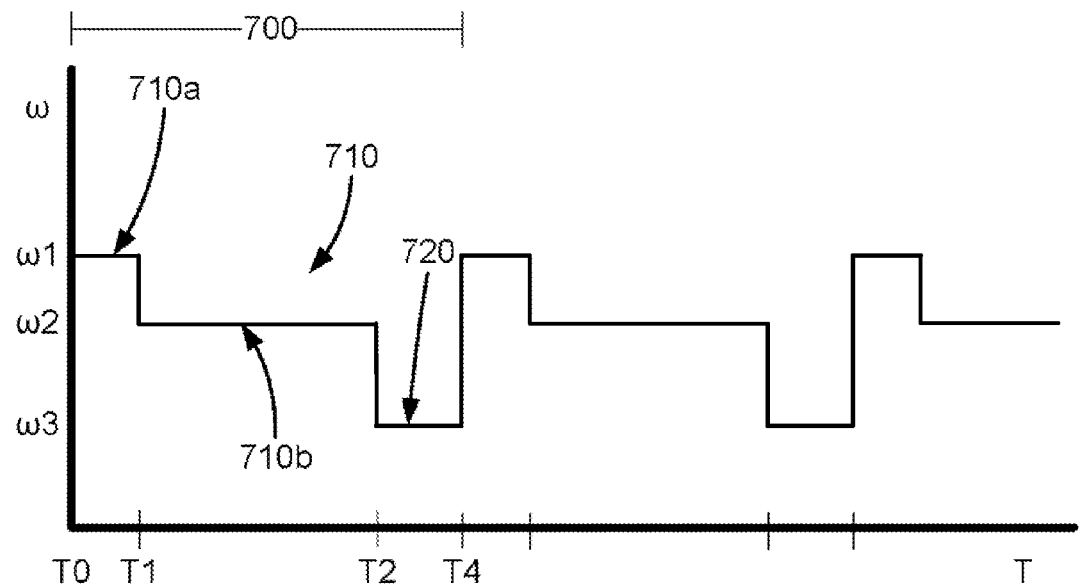
FIGS. 7 to 11 are diagrams illustrating pump speed patterns for generating an artificial pulse.

For example, the blood pump 16 can be operated to produce a pump speed pattern 700, illustrated in FIG. 7. The pump speed pattern 700 includes a first portion 710 with high pump speed producing a relatively high blood pressure, and a second portion 720 with low pump speed producing a relatively low blood pressure. Additionally, the pulsatile blood flow pattern can include a transition between the first portion 710 and the second portion 720 that produces a desired rate of pressure change in the patient's circulatory system, such as a rate of pressure change that simulates a natural physiologic pulse and that produces desired physiological effects associated with rate of pressure change. In some implementations, the rate of pressure change produced by the transition is, for example, between 500 mmHg to 1000 mmHg per second.

The first portion 710 and/or the second portion 720 of the pump speed pattern 700 can include multiple segments. In some implementations, the segments each have predetermined durations. As also shown in FIG. 7, the first high speed portion 710 of the pump speed pattern 700 includes a first segment 710a and a second segment 710b. In the first segment 710a, the rotor is rotated at a first rotation speed $\omega 1$ for a first period of time from a time T0 to a time T1. At the time T1, the rotation speed of the rotor is rapidly decreased from the first rotation speed $\omega 1$ to a second rotation speed $\omega 2$, producing a stepped transition. The rotor is rotated at the second rotation speed $\omega 2$ for a second period of time from the time T1 to a time T2 during a second segment 710b of the first portion 710 of the pump speed pattern 700. At the time T2, the rotation speed of the rotor is decreased to a third rotation speed $\omega 3$ for a third period of time from the time T2 to a time T4 during the second portion 720 of the pump speed pattern 700. This speed decrease may be as rapid as the aforementioned speed increase, or more gradual to mimic pressure changes during native diastole.

In the pump speed pattern 700, the second rotation speed $\omega 2$ is a target high blood flow pump speed, and the first rotation speed $\omega 1$ is a desired overshoot pump speed that is selected to increase the rate of change of the blood pressure during the first period. The first period of time from the time T0 to the time T1, during which the blood pump 16 is operated at the first rotation speed $\omega 1$, is shorter than the second period of time from the time T1 to the time T2, during which the blood pump 16 is operated at the second rotation speed $\omega 2$. The first period of time can be from approximately 0.01 seconds to approximately 1 second. In some implementations, the first period of time is approximately 0.05 seconds in duration. In some implementations, the first period of time can be approximately equal to, or greater than the second period of time.

Additionally, the duration of the first period can be selected to produce a desired pulse pressure, i.e., the difference between blood pressure before the speed change time T1 and during the time T1, and can be selected independently of the duration of the second period of time. The first portion 710, including the first and second time periods from the time T0 to the time T2, is longer than the second portion 720. In some implementations, the first and second time periods from the time T0 to the time T2 can be shorter than, longer than, or substantially the same duration as the second portion 720. For example, to increase the duration of pumping at the higher flow rate relative to pumping at the lower rate while still benefiting from the occasional pulse, it may be advantageous for the first portion 710 to be longer than the second portion 720. If desired, the speed of the blood pump 16 is increased to the first rotation speed $\omega 1$ and the pump speed pattern 700 can be repeated. The pump speed pattern 700 can be repeated on a continuous or discontinuous basis, and the increase of rotation speed of the rotor is also sufficiently rapid to produce a desired rate of pressure change.

The concept of overshooting the rotation speed $\omega 2$ with a greater speed, such as rotation speed $\omega 1$, is based upon partly decoupling pulse pressure, i.e. the difference between the blood pressures before and after the speed change, from the volume flow rate at the higher speed. Thus, target pulse pressures and volume flow rates can be attained at various flow conditions. Ideal values will vary with particular pump design and requirements.

As shown in FIG. 7, the period 710b can be longer than the period 710a. The period 710b can also be longer than the portion 720. In some implementations, the duration of the period 710b is more than half of the duration of the pump speed pattern 700. For example, the duration of the period 710b can be 60%, 70%, 80% or more of the duration of the pump speed pattern 700. As an alternative, depending on patient needs and pump characteristics, the duration of the period 710b can be 50% or less of the duration of the pump speed pattern 700, for example, 40%, 30%, 20% or less.

Operating the pump at the rotation speed $\omega 2$ during the period 710b can contribute to a high hydraulic efficiency during the pump speed pattern 700. During the pump speed pattern 700, the pulse pressure generated in a patient's body is generally correlated to the change in pump rotation speed, for example the magnitude of the speed change between the speeds $\omega 3$ and $\omega 1$ at time T4. Therefore, to simulate a pressure change that occurs at the beginning of systole of a physiologic pulse, a significant speed differential between the rotation speeds $\omega 3$ and $\omega 1$ is generally desired. The speed differential can be, for example, 1000 rpm, 2000 rpm, or more depending on the characteristics of the blood pump 16. Due to the magnitude of the speed differential, one or both of the speeds ω3 to ω1 may occur outside the range of highest operating efficiency of the blood pump 16.

The rotation speed ω2 can be a speed that results in a high hydraulic efficiency of the blood pump 16, for example, a speed near the middle of the operating range of the blood pump 16. During the pump speed pattern 700, the blood pump 16 can operate at the speed ω2 that results in high efficiency for a significant portion of the pump speed pattern 700, contributing to a high efficiency. As described above, the blood pump 16 can operate at the speed ω2 for more than half of the duration at the pump speed pattern 700. Thus the blood pump 16 can operate in a highly efficient manner for the majority of the pump speed pattern 700 and can also produce a pressure change that simulates the beginning of systole of a physiologic heart. Accordingly, some implementations of the pump speed pattern 700 can provide a higher efficiency than control modes that attempt to mimic all aspects of a native cardiac cycle.

The length of the period 710b relative to the length of the pump speed pattern 700 can vary based on the frequency of the artificial pulse. The duration of the period 710a and of the portion 720, by contrast, can be independent of the pulse rate. To produce the desired physiological response, a minimum duration for the period 710a and the portion 720 can be selected, for example, 0.125 seconds. The period 710b can fill the remainder of the pump speed pattern 700.

As an example, the pump speed pattern 700 can have a duration of one second, for a frequency of 60 cycles per minute. Given that the period 710a and the portion 720 have a combined duration of 0.125 seconds, the period 710b can have a duration of 0.750 seconds, or 75% of the pump speed pattern 700. As another example, when the pump speed pattern 700 has a duration of two seconds (and thus a frequency of 30 cycles per minute), the duration of the period 710b can be 1.75 seconds, which is 87.5% of the duration of the pump speed pattern 700.

In some implementations, the rotation speed ω2 is selected such that the operation of the blood pump 16 at the rotation speed ω2 produces a flow rate that has a predetermined relationship relative to the average flow rate during the pump speed pattern 700. The flow rate during the portion 710b can be within a predefined range of the average flow rate, for example, within 30% or within 10% of the average flow rate. The flow rate during the portion 710b can be substantially equal to the average flow rate.

Selecting the rotation speed ω2 to produce a flow rate that is substantially equal to the average flow rate can facilitate a transition between a pulsatile control mode and another control mode, such as a continuous flow control mode. In some implementations, the blood pump 16 operates at a particular constant speed for the greater part of the pump speed pattern 700. Operation at the constant speed can occur during, for example, the period 710b. By adjusting the speeds ω1 and ω3 and duration of the period 710a and of the portion 720, the average pump volume flow rate can be tuned to substantially match an average pump volume flow rate that would be realized in a different optional setting. Consequently, a clinician or patient can switch from an artificial pulse mode to another control mode in a manner that causes only a small difference or no difference in average volume flow rate. This can provide a clinical advantage when the artificial pulse is a selectable option among at least one alternative, for example, a constant speed option.

As an example, a speed set by a clinician for a constant speed mode can also be utilized for a constant speed portion of an artificial pulse mode. The speed can be selected by the clinician to produce a desired volume flow rate through the blood pump 16 during the constant speed mode (e.g., during continuous flow or non-pulsatile operation of the blood pump 16). In the artificial pulse mode, the same selected speed can be used as, for example, the rotation speed ω2 during the period 710b of the pump speed pattern 700. The speeds ω1, ω3 and the duration of the period 710a and the portion 720 are calculated or chosen to approximately balance the volume flow rate for the pump speed pattern 700. For example, the reduced flow rate during the portion 720 can offset the increased flow rate during the portion 710a. As a result, the net volume flow rate during the pump speed pattern 700 can substantially match the volume flow rate during the constant speed mode. Thus in either the constant speed mode or the artificial pulse mode, the volume flow rate can be approximately the same, permitting the clinician to switch from one mode to another without affecting the volume flow rate. This can help avoid potentially dangerous conditions that could occur if switching from one mode to another resulted in sudden changes in flow rate. For example, a sudden decrease in volume flow rate could cause acutely insufficient perfusion for the patient, and a sudden increase in volume flow rate could cause ventricular suction and arrhythmia.

Figure 8:
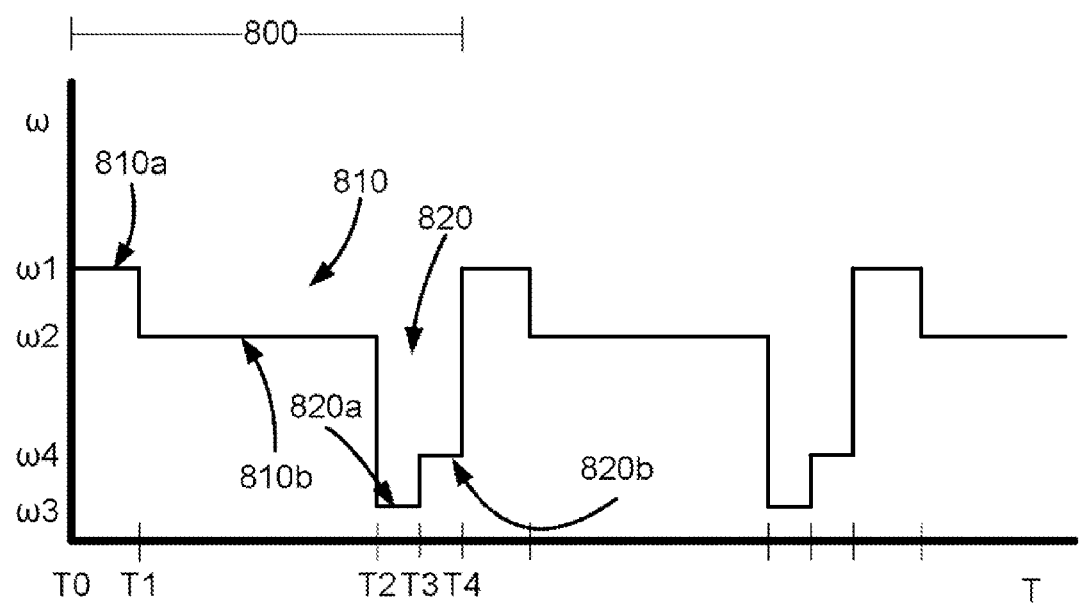

As mentioned above, the second portion 710 of the pump speed pattern 700 can also include multiple segments. For example, as shown in FIG. 8, a pump speed pattern 800 includes a first portion 810 that has a first segment 810a and a second segment 810b and the pump speed pattern 800 includes a second portion 820 that has a first segment 820a and a second segment 820b. During the first segment 810a, from the time T0 to the time T1, the blood pump 16 is operated at the first rotation speed ω1. At the time T1, the speed of the blood pump 16 is reduced to the second rotation speed ω2, and the blood pump 16 is operated at the second rotation speed ω2 for the second period of time from the time T1 to the time T2. At the time T2, the speed of the blood pump 16 is reduced from the second speed ω2 to the third rotation speed ω3. The blood pump 16 is operated at the third rotation speed ω3 for a third period of time from the time T2 to a time T3 during a first segment 820a of the second portion 820 of the pump speed pattern 800. At the time T3, the speed of the blood pump 16 is increased from the third rotation speed ω3 to a fourth rotation speed ω4, and the blood pump 16 is operated at the fourth rotation speed ω4 during a fourth period of time from the time T3 to the time T4 during a second segment 820b of the second portion 820 of the pump speed pattern 800. If desired, the speed of the blood pump 16 is increased to the first rotation speed ω1 and the pump speed pattern 800 can be repeated. The pump speed pattern 800 can be repeated on a continuous or discontinuous basis, and the increase of rotation speed of the rotor is also sufficiently rapid to produce a desired rate of pressure change.

Similar to the concept of overshooting ω2 in pattern 700, the concept of overshooting the rotation speed ω4 with a lower rotation speed, such as the rotation speed ω3, is also based upon decoupling pulse pressure from the volume flow rate at the lower rotation speed ω4. Thus, the pump speed pattern 800 more completely decouples target pulse pressures and volume flow rates than the pump speed pattern 700, and ideal values can be attained, or more closely approximated, at various flow conditions.

While a single overshoot pump speed for a transition between pump speeds are illustrated and described with reference to FIGS. 7 and 8, multiple overshoot pump speeds for one or more transitions can be used. For example, FIG.

9 illustrates a pump speed pattern 900 that includes multiple overshoot pump speeds for each transition. The pump speed pattern 900 includes a first portion 910 having a first segment 910a and a second segment 910b, and that includes a second portion 920 having a first segment 920a and a second segment 920b. The first segment 910a of the first portion 910 of the pump speed pattern 900 includes a first step 931 during which the blood pump 16 is operated at the first rotation speed ω1 to overshoot the target pump speed ω2 and a second transition step 433 during which time the blood pump 16 is operated at a fifth speed ω5 to transition from the first rotation speed ω1 to the second rotation speed ω2. Similarly, the first segment 920a of the second portion 920 includes a first step 941 during which the blood pump 16 is operated at the third rotation speed ω3 and a second segment 443 during which the blood pump 16 is operated at a sixth speed ω6 to transition between the third speed ω3 and the fourth rotation speed ω4. If desired, the speed of the blood pump 16 is increased to the first rotation speed ω1 and the pump speed pattern 900 can be repeated. The pump speed pattern 900 can be repeated on a continuous or discontinuous basis, and the increase of rotation speed of the rotor is also sufficiently rapid to produce a desired rate of pressure change.

The concept of creating multiple stepwise rotation speed changes is based upon producing the physiologic response that is similar to that produced during human cardiac systole and diastole. This is distinct from mimicking the nature of a native pulse waveform in its entirety. As described above, greater hydraulic efficiency can often be achieved by avoiding imitation of the physiologic pressure waveform over the pulse cycle. It was previously mentioned that an artificial pulse offers a multitude of potential clinical advantages. For some or all of these potential clinical advantages, the benefit of closely matching the energy dissipated during a healthy native pulse varies. To the extent that close matching facilitates achieving these potential clinical advantages, the additional complexity of pattern 900 may be warranted.

Figure 9:
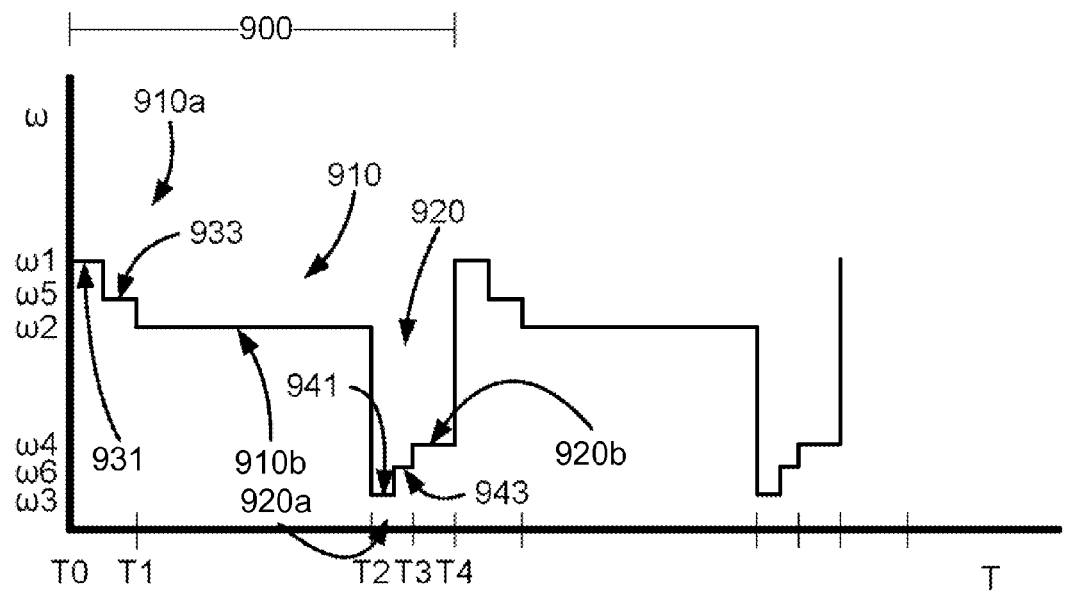
Figure 10:
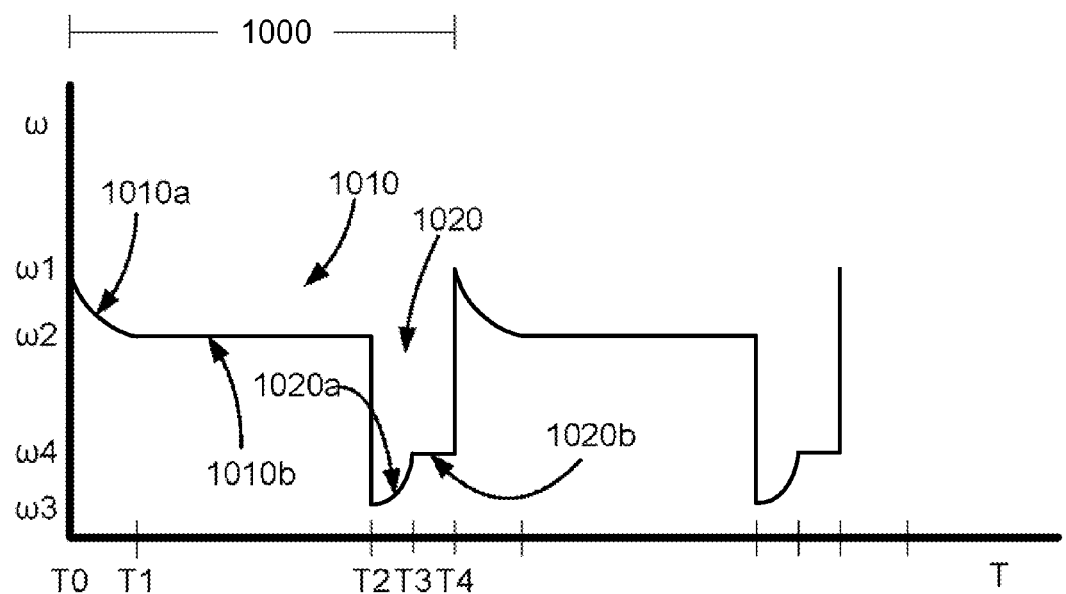

In contrast to the stepped or discontinuous transitions discussed above with respect to FIGS. 7 to 9, smooth or continuous transitions may be used in place of, or in combination with, stepped transitions between different pump operation speeds. For example, smooth transitions are illustrated in the pump speed pattern 1000 of FIG. 10. The pump speed pattern 1000 includes a first portion 1010 and a second portion 1020. The first portion 1010 includes a first segment 1010a during which the speed of the pump 16 is decreased gradually, at a strategically-selected rate, from the first rotation speed ω1 to the second rotation speed ω2 from the time T0 to the time T1. The selected rate of pump speed decrease can be, for example, a particular linear rate or a particular non-linear rate. During the second segment 1010b of the first portion 1010, from the time T1 to the time T2, the blood pump 16 is operated at the second rotation speed ω2. Similarly, the second portion 1020 includes a first segment 1020a during which the speed of the blood pump 16 is increased gradually, at a strategically-selected rate, from the third rotation speed ω3 to the fourth rotation speed ω4 from the time T2 to the time T3. During the second segment 1020b of the second portion 1020, from the time T3 to the time T4, the blood pump 16 is operated at the fourth rotation speed ω4. If desired, at time T4, there is a step increase in the rotation speed of the rotor can be rapidly increased to the first rotation speed ω1, and the pump speed pattern 1000 is repeated.

The concept of creating multiple speed changes at a strategically-selected rate is based upon producing the physiologic response that is similar to that produced during human cardiac systole and diastole. For example, if very accurate matching of energy dissipation during a human pulse is necessary, the additional complexity of pattern 1000 may be warranted.

The pump speed pattern 1000 illustrates the difference between stepped transitions discussed above with respect to pump speed patterns 700-900, produced by rapidly changing the rotation speed of the rotor, and the gradual transitions of the first segment 1010a of the first portion 1010 and the first segment 1020a of the second portion 1020 of the pump speed pattern 1000. Such gradual transitions can be included, for example, to mimic pressure changes exhibited during native diastole, as may be achieved by the gradual transition of the first segment 1010a of the first portion 1010 of the pump speed pattern 1000. In some implementations, one or more of the rotation speed decreases of a pump speed pattern can be gradual transitions. For example, a pump speed pattern can include a gradual decrease in rotation speed from the first rotation speed ω1 to the third rotation speed ω3 and a stepped transition from the third pump speed ω3 back to the first rotation speed ω1. Various combinations of stepped and gradual transitions can be included in a pump speed pattern to produce a desired arterial pressure wave form, or other desired physiologic effect. Additionally, the type of transition between rotation speeds can affect power consumption of the blood pump 16, and the pump speed pattern can be selected based, at least in part, on power consumption considerations.

For all the pump speed patterns discussed it should be appreciated that although rotor speed is the technological parameter utilized to impart an artificial pulse, any physiologic effect is related to the consequential pressure and flow patterns, including pulse pressure, the maximum time variation in rate of blood pressure change (dp/dt), and the like. Rotor speed is not intrinsically physiologically meaningful. The human vascular system naturally dampens the native pulse produced by the heart, and it will do the same for an artificial pulse produced as described. The invention describes a utilitarian combination of factors that result in a physiological meaningful pulse. Thus, the pump speed patterns 700-1000 described above are exemplary combinations of parameters that result in a physiologically meaningful pulse.

The controller 20 can generate an artificial pulse with one of the pumps 16, 18 while the pump 16, 18 is controlled based on pulsatility index calculations. The controller 20 can thus implement pulsatility index control and artificial pulse control concurrently for a single pump 16, 18. As described above, pulsatility index calculations for one of the ventricles 12, 14 can be used to dynamically set a speed for one or both of the pumps 16, 18. The pump speed can be adjusted in response to changing physiologic conditions that are reflected in the pulsatility index. An artificial pulse according to one of the waveforms 700-1000 can be generated while pump speed is regulated based on pulsatility index measurements.

Figure 11:
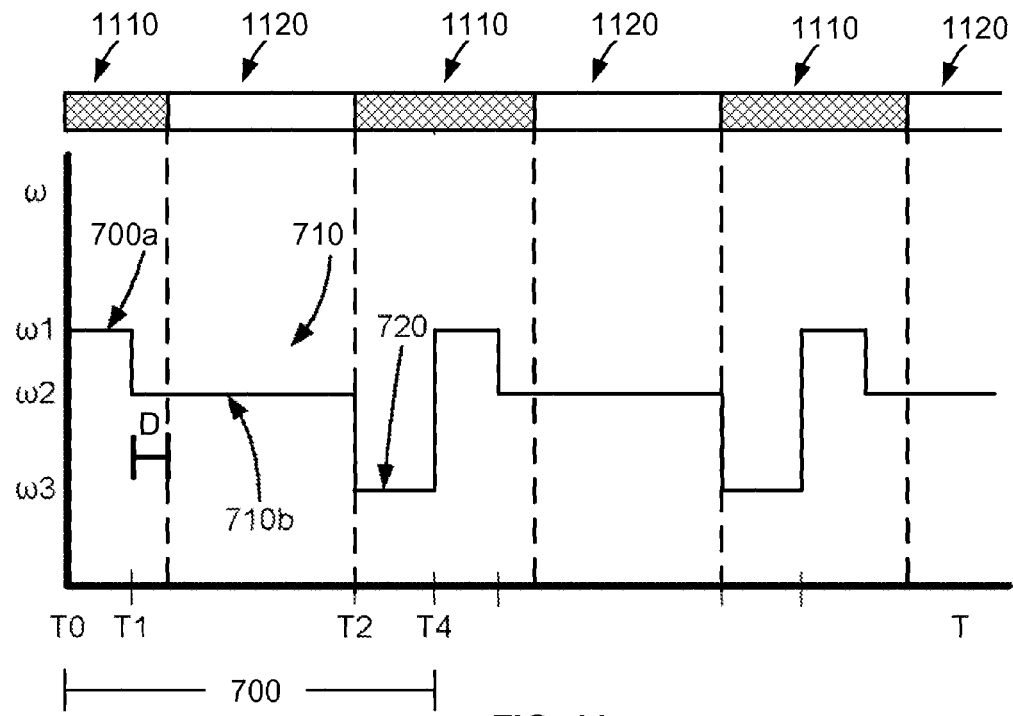

Referring to FIG. 11, the pump speed pattern 700 is produced by the left blood pump 16 while the blood pump 16 is controlled at least in part based on the left pulsatility index, PIL. To combine pulsatility index control and artificial pulse generation, the controller 20 determines a speed for the pump 16 using the pulsatility index, PIL, as described above. The controller 20 sets the determined speed as the rotation speed ω2. As the pulsatility index changes in response to changing physiologic conditions, the controller 20 adjusts the rotation speed ω2 in the same manner that the controller 20 adjusts the pump speed during a continuous flow control mode.

In some implementations, the controller 20 sets the speeds ω1 and ω3 and the durations of the period 710a and the portion 720 to maintain a volume flow rate for the pump speed pattern 700 that is substantially equal to the volume flow rate produced during operation of the pump 16 at the rotation speed ω2. As the controller 20 adjusts the rotation speed ω2 based on changes in the pulsatility index, the controller 20 also adjusts the speeds ω1 and ω3 to maintain an appropriate average flow rate. As a result, the average volume flow rate produced during the pump speed pattern 700 corresponds to the average volume flow rate that would be produced using continuous flow control at the rotation speed ω2.

Because changes in blood flow caused by the pump speed pattern 700 can interfere with the accuracy of pulsatility index calculations, the controller 20 calculates the pulsatility index using blood flow rates measured during selected portions of the pump speed pattern 700. For example, the controller 20 calculates the pulsatility index using blood flow measured during a period in which the pump 16 is operated at a constant speed. As a result, the effects of the artificially generated pulse are excluded from the pulsatility index calculations.

For the pulsatility index calculations, the controller 20 uses measurements of the blood flow that occurs during a period 1120. The period 1120 occurs during the period 710a, during which the pump 16 is operated at the speed ω2. In particular, the period 1120 begins at a time after the time T1, and the period 1120 can extend to the time T2, just before the pump speed is changed. The beginning of the period 1120 occurs at a delay D after time T1, permitting the flow rate through the pump to stabilize after the speed change at time T1. The delay D can have a duration of, for example, 0.05 seconds or 0.1 seconds.

To calculate the pulsatility index, the controller 20 excludes measurements of blood flow through the pump 16 outside the period 1120. For example, the controller 20 can ignore or not measure blood flow rates during an excluded period 1110. The excluded period 1110 includes the period 720a and the portion 720, during which the artificial pulse can obscure the changes in flow rates due to the pulsatility of the ventricle 12. As shown, the excluded period 1110 and the period 1120 alternate such that the periods 1120 are interleaved between the excluded periods 1110.

The controller 20 synchronizes the timing of measurements for pulsatility index calculation with the timing of the pump speed pattern 700. For example, when blood flow is measured using the current draw or power consumption of the pump 16, the controller 20 uses only current or power measurements corresponding to pump activity during the 1120. Similarly, when blood flow is measured using inflow pressure sensors, outflow pressure sensors, or flow sensors, only sensor data received within the period 1120 is used. Thus data that is influenced by artificial blood flow variations caused by the artificial pulse are excluded from the pulsatility index calculations.

In some implementations, the controller 10 increases the likelihood that a natural physiologic pulse coincides with the period 1120 by generating the artificial pulse at a non-physiologic rate. In some implementations, the artificial pulse is generated at a rate lower than 50 beats per minute, for example, at 30 beats per minute. At pulse rates below typical physiologic heart rates, each repetition of the pump speed pattern 700 can include an entire physiologic pulse cycle, and can also include a fraction or more of an additional cycle. Two or more complete natural pulse cycles can occur during the pump speed pattern 700.

At pulse rates below typical physiological rates, the period 710a and thus the period 1120 comprise a larger portion of the pump speed pattern 700, increasing the likelihood that each period 1120 will include at least one complete natural pulse cycle. The duration of the period 1120 can be one second or more. As an example, at an artificial pulse rate of 30 beats per minute, the period 710a can have a duration of 1.75 seconds, permitting a period 1120 of 1.70 seconds. Alternatively, periods 1120 that have a duration of less than one second can also be used. Even though each period 1120 may not include a complete natural pulse cycle, averages of pulsatility index calculations for multiple periods 1120 or maximum or minimum rates across multiple periods 1120 can be used to produce an accurate indication of pulsatility of the ventricle.

In some implementations, the controller 20 synchronizes the pump speed pattern 700 with the physiologic pulse rate. Thus the controller 20 can time the period 1120 to include at least one natural pulse cycle, to include multiple natural pulse cycles, or to consistently include a particular portion of a natural pulse cycle. For example, the artificial pulse may be generated at half of the pulse rate of the natural heart, and the timing of the pump speed pattern 700 can be set such that each period 1120 includes a complete natural pulse cycle. The pump speed pattern 700 can be synchronized such that successive periods 1120 include every other natural pulse cycle of the patient. Other synchronizations can also be used, for example, such that successive periods 1120 including every third natural pulse cycle, or such that periods 1120 each include two consecutive natural pulse cycles.

Figure 12:
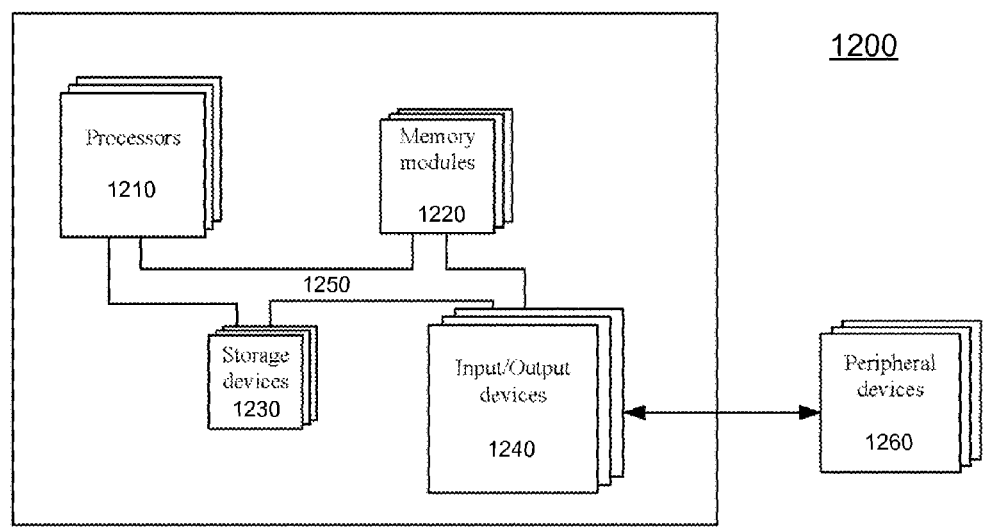
FIG. 12 is a diagram of a computer system.

In use, the pump speed patterns 700-1000 can be generated by the controller 20, which is configured to generate an electrical drive signal to operate the blood pump 16. For example, the controller 20 can include a computer system 1200, shown in FIG. 12, that outputs an electrical current to operate the blood pump 16. In order to produce the pump speed pattern 700 described above, the controller 20 outputs a first electrical current from the time T0 to the time T1. At the time T1, the controller 20 reduces the output electrical current to a second current that is lower than the first electrical current, and outputs the second electrical current from the time T1 to the time T2. At the time T2, the controller 20 reduces the output electrical current from the second current to a third current, and outputs the third electrical current from the time T2 to the time T4.

The computer system 1200 includes one or more processors 1210, memory modules 1220, storage devices 1230, and input/output devices 1240 connected by a system bus 1250. The input/output devices 1240 are operable to communicate signals to, and/or receive signals from, one or more peripheral devices 1260. For example, a peripheral device 1260 can be used to store computer executable instructions on the memory modules 1220 and/or the storage devices 1230 that are operable, when executed by the processors, to cause the controller 20 to generate a waveform to control the operation of the pump 16 and produce a pump speed pattern, such as the pump speed patterns 700-1000.

Additionally, the controller 20 can include a sensor that provides a signal that indicates activity of the heart. For example, the controller 20 can include a sensor that provides a signal indicative of power consumption of the blood pump 16. The signal can be used to determine when the left ventricle 12 contracts. For example, the power consumption of the blood pump 16 may, for a given operating speed, increase as the left ventricle 12 contracts. Based on the determined heart activity, the controller 20 can adjust the generated control waveform. For example, the controller 20 can automatically adjust the timing and duration of the first portion 710 and the second portion 720 of the pump speed pattern 700 such that the first portion 710 approximately coincides with a contraction of the left ventricle 12. The pump 16 is controlled such that the time T0 approximately coincides with a beginning of a contraction of the left ventricle 12 and the time T2 approximately coincides with an end of the contraction of the left ventricle 12. The time T4 approximately coincides with a beginning of a subsequent contraction of the left ventricle 12. Thus, the durations of the various portions and/or segments of the pump speed patterns described above can be changed individually or collectively for one or more repetitions of the pump speed patterns. Using these techniques, the controller 20 can synchronize the pulsatile operation of the pump with the natural physiologic pulse of the heart.

Alternatively, the controller 20 can generate the control waveform independently of the activity of the heart and/or to operate in opposition to the activity of the heart, such as where the first portion 710 occurs during left ventricular relaxation. Similarly, the controller 20 can generate a control waveform that includes a distinctly non-physiologic pulse rate, such as fewer than 40 high-pressure periods per minute, and the waveform can be generated independently of native heart function. In some examples, the blood pump 16 can be operated to produce distinctly physiologic pulse rates, such as between 50 and 110 high-pressure periods per minute, and can be controlled dependently or independently of heart function.

A number of implementations have been described. Nevertheless, it will be understood that various modifications may be made without departing from the spirit and scope of the claimed invention. For example, the pump speed patterns described above can be used with various types of blood pumps, including axial flow blood pumps and centrifugal flow blood pumps. Similarly, the rotors of blood pumps used to produce pulsatile blood flow patterns as described above may be electromagnetically-suspended, hydraulically-suspended, mechanically-suspended, or combinations thereof. The rotors may also partially be passively magnetically-suspended. However, the effect of an artificial pulse may most accurately be simulated by a pump in which the rotor is electromagnetically suspended, with or without partial passive magnetic suspension, because in general, other things being equal, electromagnetic suspension yields a high degree of responsiveness of the rotor to speed change inputs. For example, mechanical bearings associated with mechanical suspension and/or very narrow rotor clearance gaps associated with hydraulic suspension hinder rapid acceleration of the rotor compared to similar pumps that employ electromagnetic suspension. Additionally, while the pump speed patterns described above have been described with regard to a measure of angular velocity, the pump speed patterns can be produced with regard to one or more different measures of pump speeds. Additionally, there may be a delay between a change in drive signal generated by the controller 20 and a change in operating speed of the blood pump. Thus, the controller 20 can be operated such that changes in the output drive signal are effected at a time to produce a corresponding change in pump operating speed at a desired time, such as a time that approximately coincides with selected activity of the heart.

In some implementations, the pump speed patterns 700-1000 can include additional portions or segments during which the blood pump is operated at other speeds. For example, at desired times, the blood pump can be operated to produce a pump speed pattern that produces a desired physiologic effect, such as opening or closing the aortic valve. Such operation of the blood pump can interrupt a generally continuous repetition of a selected one or more of the pump speed patterns described above, or others, including an indefinite period of constant speed, and a selected pump speed pattern can be resumed after the desired physiologic effect has been produced. The pump speed patterns 700-1000 can also include different portions or segments. For example, the second segment 710*b* of the first portion 710 of the pump speed pattern 700 can include multiple pump speeds. Similarly, the transitions between pump speeds, such as the reduction in pump speed from the first rotation speed $\omega 1$ to the second rotation speed $\omega 2$, can include constant, variable, exponential, combinations thereof, or other rate of speed change over time such that the transition, such as the first segment 1010*a* of the first portion 1010 of the pump speed pattern 1000, is linear, curvilinear, parabolic, logarithmic, sinusoidal, stepped, or combinations thereof.

In some implementations, one or more of the pump speed changes in the pump speed patterns 700-1000 can be monotonic. A transition from one speed to another may occur gradually over a period of time, yet change directly from one speed to another. For example, to decrease a pump speed from a first rotational speed to a second rotational speed, the controller 20 can reduce the pump speed without causing an intervening period of increasing pump speed. Similarly, the transition from the first rotational speed to the second rotational speed can occur without operating the pump above the first rotational speed during the transition.

Additionally, a blood pump can be operated according to a pump speed pattern that is selected according to a pump power consumption rate associated with the pump speed pattern, a pump efficiency associated with the pump speed pattern, a blood flow rate associated with the pump speed pattern, and/or a rate of blood pressure change associated with the pump speed pattern. For example, in a first mode, the controller 20 can be operated to produce a pump speed pattern that produces a desired rate of blood pressure change. When a low power condition is detected, the controller 20 can be switched to a power-saving mode to produce a pump speed pattern that has a low power consumption rate, even if the desired rate of pressure change is not produced in the power-saving mode.

A number of implementations have been described. Nevertheless, it will be understood that various modifications may be made without departing from the spirit and scope of the claimed invention. For example, the pump speed patterns described above can be used with various types of blood pumps, including axial flow blood pumps and centrifugal flow blood pumps. Similarly, the rotors of blood pumps used to produce pulsatile blood flow patterns as described above may be electromagnetically-suspended, hydraulically-suspended, mechanically-suspended, or combinations thereof. The rotors may also partially be passively magnetically-suspended. However, the effect of an artificial pulse may most accurately be simulated by a pump in which the rotor is electromagnetically suspended, with or without partial passive magnetic suspension, because in general, other things being equal, electromagnetic suspension yields a high degree of responsiveness of the rotor to speed change inputs. For example, mechanical bearings associated with mechanical suspension and/or very narrow rotor clearance gaps associated with hydraulic suspension hinder rapid acceleration of the rotor compared to similar pumps that employ electromagnetic suspension. Additionally, while the pump speed patterns described above have been described with regard to a measure of angular velocity, the pump speed patterns can be produced with regard to one or more different measures of pump speeds. Additionally, there may be a delay between a change in drive signal generated by the controller 20 and a change in operating speed of the blood pump. Thus, the controller 20 can be operated such that changes in the output drive signal are effected at a time to produce a corresponding change in pump operating speed at a desired time, such as a time that approximately coincides with selected activity of the heart.

In some implementations, the pump speed patterns 700 to 1000 can include additional portions or segments during which the blood pump is operated at other speeds. For example, at desired times, the blood pump can be operated to produce a pump speed pattern that produces a desired physiologic effect, such as opening or closing the aortic valve. Such operation of the blood pump can interrupt a generally continuous repetition of a selected one or more of the pump speed patterns described above, or others, including an indefinite period of constant speed, and a selected pump speed pattern can be resumed after the desired physiologic effect has been produced. The pump speed patterns 700 to 1000 can also include different portions or segments. For example, the second segment 710$b$ of the first portion 710 of the pump speed pattern 700 can include multiple pump speeds. Similarly, the transitions between pump speeds, such as the reduction in pump speed from the first rotation speed $\omega 1$ to the second rotation speed $\omega 2$, can include constant, variable, exponential, combinations thereof, or other rate of speed change over time such that the transition, such as the first segment 1010$a$ of the first portion 1010 of the pump speed pattern 1000, is linear, curvilinear, parabolic, logarithmic, sinusoidal, stepped, or combinations thereof.

In some implementations, the pump speed changes in the pump speed pattern 700 can be monotonic. A transition from one speed to another may occur gradually over a period of time, yet change directly from one speed to another. For example, to decrease a pump speed from a first rotational speed to a second rotational speed, the controller 20 can reduce the pump speed without causing an intervening period of increasing pump speed. Similarly, the transition from the first rotational speed to the second rotational speed can occur without operating the pump above the first rotational speed during the transition.

Additionally, a blood pump can be operated according to a pump speed pattern that is selected according to a pump power consumption rate associated with the pump speed pattern, a pump efficiency associated with the pump speed pattern, a blood flow rate associated with the pump speed pattern, and/or a rate of blood pressure change associated with the pump speed pattern. For example, in a first mode, the controller 20 can be operated to produce a pump speed pattern that produces a desired rate of blood pressure change. When a low power condition is detected, the controller 20 can be switched to a power-saving mode to produce a pump speed pattern that has a low power consumption rate, even if the desired rate of pressure change is not produced in the power-saving mode.

As mentioned above, in some implementations, the blood pumps 16, 18 can be used to assist a patient's heart during a transition period, such as during a recovery from illness and/or surgery or other treatment. In other implementations, the blood pumps 16, 18 can be used to partially or completely replace the function of the patient's heart on a generally permanent basis.

The subject matter and the functional operations described in this specification can be implemented in digital electronic circuitry, in tangibly-embodied computer software or firmware, in computer hardware, including the structures disclosed in this specification and their structural equivalents, or in combinations of one or more of them. The subject matter described in this specification can be implemented as one or more computer programs, i.e., one or more modules of computer program instructions encoded on a tangible non transitory program carrier for execution by, or to control the operation of, data processing apparatus. The program carrier can be a computer storage medium, for example, a machine-readable storage device, a machine-readable storage substrate, a random or serial access memory device, or a combination of one or more of them, as described further below. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read only memory or a random access memory or both. The essential elements of a computer are a processing unit for performing or executing instructions and one or more memory devices for storing instructions and data. A computer can also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a pump, a pump controller, or a portable storage device, e.g., a universal serial bus (USB) flash drive or other removable storage module, to name a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

A number of implementations have been described. Nevertheless, it will be understood that various modifications may be made without departing from the spirit and scope of the disclosure.

What is claimed is:

1. A blood pump system, comprising:
a first rotary blood pump configured to be connected to a patient's left ventricle to pump blood from the left ventricle to the patient's ascending aorta via a first outflow graft;
a second rotary blood pump configured to be connected to a patient's right ventricle to pump blood from the right ventricle to the patient's pulmonary system via a second outflow graft; and
a blood pump controller including:
an input interface configured to:
receive a first signal indicative of blood flow rate through a first rotary blood pump configured to be connected to a patient's left ventricle and pump blood from the left ventricle to the patient's ascending aorta via a first outflow graft; and
receive a second signal indicative of blood flow rate through a second rotary blood pump different from the first rotary blood pump and configured to be connected to the patient's right ventricle and pump blood from the right ventricle to the patient's pulmonary system via a second outflow graft; and
a processing unit configured to generate and transmit separate control signals to the first and second rotary blood pumps to adjust the speed of each of the first and second rotary blood pumps based on a target support level for the patient while maintaining a predetermined ratio between blood flow rate through the second rotary blood pump and blood flow rate through the first rotary blood pump.

2. The blood pump system of claim 1, wherein the processing unit is further configured to:
generate a target pulsatility index for the first rotary blood pump based on the target support level for the patient;
measure a pulsatility-index for the patient's left ventricle; and
control the speed of the first rotary blood pump to minimize a difference between the measured pulsatility index for the left ventricle and the target pulsatility index for the first rotary blood pump.

3. The blood pump system of claim 2, wherein the measured pulsatility index indicates a load on the patient's left ventricle experienced during contraction of the left ventricle.

4. The blood pump system of claim 2, wherein the measured pulsatility index (PI) is calculated by the processing unit over a control interval according to the following equation: $PI=(Q_{max}-Q_{min})/Q_{ave}$, where $Q_{max}$ is a maximum flow rate through the first rotary blood pump in the control interval, $Q_{min}$ is a minimum flow rate through the first rotary blood pump in the control interval, and $Q_{ave}$ is an average flow rate through the first pump over the control interval.

5. The blood pump system of claim 4, wherein the processing unit is further configured to:
control at least one of the first and second pumps to produce an artificially induced pulsatile blood flow; and
calculate the measured pulsatility index such that data influenced by artificial blood flow variations of the artificially induced pulsatile blood flow are excluded from the calculation of the measured pulsatility index.

6. The blood pump system of claim 2, wherein the processing unit is further configured to control the speed of the first rotary blood pump based on a detected heart rate so as to:
decrease the speed of the first rotary blood pump when the measured pulsatility index is below the target pulsatility index and the detected heart rate does not exceed a threshold heart rate;
maintain the speed of the first rotary blood pump when the measured pulsatility index is below the target pulsatility index and the detected heart rate exceeds the threshold heart rate; and
increase the speed of the first rotary blood pump when the measured pulsatility index is above the target pulsatility index.

7. The blood pump system of claim 1, wherein the processing unit is further configured to:
generate a target pulsatility index for the second rotary blood pump based on the target support level for the patient;
measure a pulsatility index for the patient's right ventricle; and
control the speed of the second rotary blood pump to minimize a difference between the measured pulsatility index for the right ventricle and the target pulsatility index for the second rotary blood pump.

8. The blood pump system of claim 1, wherein the processing unit is configured to control at least one of the first and second rotary blood pumps to operate in a pulse mode that simulates a pressure change of natural physiologic pulse.

9. The blood pump system of claim 8, wherein controlling the rotary blood pump to operate in the pulse mode comprises:
increasing the operating speed of the rotary blood pump from a first speed to a second speed; and
decreasing the operating speed of the rotary blood pump from the second speed to a third speed that is greater than the first speed.

10. The blood pump system of claim 8, wherein controlling the rotary blood pump to operate in the pulse mode comprises:
operating the rotary blood pump at a first speed for a first period of time;

reducing the speed of the rotary blood pump from the first speed to a second speed;
operating the rotary blood pump at the second speed for a second period of time;
reducing the speed of the rotary blood pump from the second speed to a third speed;
operating the rotary blood pump at the third speed for a third period of time; and
increasing the speed of the rotary blood pump from the third speed to the first speed.

11. The blood pump system of claim 1, wherein the processing unit is further configured to alternately control at least one of the first and second rotary blood pumps between a pulse mode that simulates a pressure change of natural physiologic pulse and a continuous mode that does not simulate a pressure change of natural physiologic pulse.

12. The blood pump system of claim 11, wherein the processing unit is configured to control one of the first and second rotary blood pumps to operate in the pulse mode while controlling the other of the first and second rotary blood pumps to operate in the continuous mode.

13. The blood pump system of claim 1, wherein the processing unit is further configured to control the speed of the first pump based on a detected heart rate.

14. The blood pump system of claim 1, wherein the received signal indicating blood flow rate through the first rotary blood pump is indicative of a degree of cardiac unloading.

15. A method of controlling blood flow, comprising:
operating a first rotary blood pump connected to a patient's left ventricle to pump blood from the left ventricle to the patient's ascending aorta via a first outflow graft;
operating a second rotary blood pump connected to a patient's right ventricle to pump blood from the right ventricle to the patient's pulmonary system via a second outflow graft; and
separately controlling each of the first and second rotary blood pumps via a blood pump controller to provide a target support level for the patient while maintaining a predetermined ratio between blood flow rate through the second rotary blood pump and blood flow rate through the first rotary blood pump.

16. The method of claim 15, wherein:
the blood pump controller controls the speed of the second rotary blood pump such that the blood flow rate through the second rotary blood pump is less than the blood flow rate through the first rotary blood pump.

17. The method of claim 15 further comprising:
determining, by the blood pump controller, that the measured blood flow rate through the first pump has changed to a new first pump blood flow rate; and
adjusting, by the blood pump controller, the speed of second pump to maintain the predetermined ratio between the blood flow rate through the second rotary blood pump and the new first pump blood flow rate.

18. The method of claim 15 further comprising:
determining, by the blood pump controller, that the measured blood flow through one of the first and second rotary blood pumps exceeds a threshold; and
controlling, by the blood pump controller, the speed of each of the first and second rotary blood pumps such that the measured blood flow that exceeds the threshold is reduced below the threshold.

19. The method of claim 15, further comprising controlling, by the blood pump controller, one of the first and second rotary blood pumps to generate a rate of pressure change that simulates a pressure change of natural physiologic pulse.

20. The method of claim 19, wherein generation of the rate of pressure change that simulates a pressure change of natural physiologic pulse comprises:
increasing the operating speed of said one of the rotary blood pumps from a first speed to a second speed; and
decreasing the operating speed of the rotary blood pump from the second speed to a third speed that is greater than the first speed.

21. The method of claim 19, wherein generation of the rate of pressure change that simulates a pressure change of natural physiologic pulse comprises:
operating said one of the rotary blood pumps at a first speed for a first period of time;
reducing the speed of said one of the rotary blood pumps from the first speed to a second speed;
operating said one of the rotary blood pumps at the second speed for a second period of time;
reducing the speed of said one of the rotary blood pumps from the second speed to a third speed;
operating said one of the rotary blood pumps at the third speed for a third period of time; and
increasing the speed of said one of the rotary blood pumps from the third speed to the first speed.

22. The method of claim 19, comprising alternately controlling at least one of the first and second rotary blood pumps in a pulse mode that simulates a pressure change of natural physiologic pulse and a continuous mode that does not simulate a pressure change of natural physiologic pulse.

23. The method of claim 22, comprising controlling one of the first and second rotary blood pumps to operate in the pulse mode while controlling the other of the first and second rotary blood pumps to operate in the continuous mode.

24. The method of claim 15, further comprising:
generating, by the blood pump controller, a target pulsatility index for the first rotary blood pump based on the target support level for the patient;
measuring, by the blood pump controller, a pulsatility value for the patient's left ventricle; and
controlling, by the blood pump controller, the speed of the first rotary blood pump to minimize a difference between the measured pulsatility index for the left ventricle and the target pulsatility index for the first rotary blood pump.

25. The method of claim 24, wherein the measured pulsatility index (PI) is calculated by the blood pump controller over a control interval according to the following equation: $PI=(Q_{max}-Q_{min})/Q_{ave}$, where $Q_{max}$ is a maximum flow rate through the first pump in the control interval, $Q_{min}$ is a minimum flow rate through the first rotary blood pump in the control interval, and $Q_{ave}$ is an average flow rate through the first rotary blood pump over the control interval.

26. The method of claim 24, further comprising:
controlling, by the blood pump controller, at least one of the first and second rotary blood pumps to produce an artificially induced pulsatile blood flow; and
calculating, by the blood pump controller, the measured pulsatility index such that data influenced by artificial blood flow variations of the artificially induced pulsatile blood flow are excluded from the calculation of the measured pulsatility index.

27. The method of claim 24, further comprising:
- decreasing the speed of the first pump when the measured pulsatility index is below the target pulsatility index and the detected heart rate does not exceed a threshold heart rate;
- maintaining the speed of the first pump when the measured pulsatility index is below the target pulsatility index and the detected heart rate exceeds the threshold heart rate; and
- increasing the speed of the first pump when the measured pulsatility index is above the target pulsatility index.

28. The method of claim 15, comprising controlling the speed of the first pump based on a detected heart rate.

29. The method of claim 15, wherein measuring the blood flow rate through the first rotary blood pump comprises processing a signal indicative of a degree of cardiac unloading.

\* \* \* \* \*